United States Patent
Sambai

(10) Patent No.: US 10,851,052 B2
(45) Date of Patent: Dec. 1, 2020

(54) METHOD FOR PRODUCING MERCAPTOPHENOL COMPOUND AND INTERMEDIATE OF SAID COMPOUND

(71) Applicant: KUMIAI CHEMICAL INDUSTRY CO., LTD., Tokyo (JP)

(72) Inventor: Kazuhiro Sambai, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 16/761,099

(22) PCT Filed: Feb. 22, 2019

(86) PCT No.: PCT/JP2019/006674
§ 371 (c)(1),
(2) Date: May 1, 2020

(87) PCT Pub. No.: WO2019/167814
PCT Pub. Date: Sep. 6, 2019

(65) Prior Publication Data
US 2020/0277257 A1    Sep. 3, 2020

(30) Foreign Application Priority Data

Feb. 27, 2018   (JP) ................. 2018-033523

(51) Int. Cl.
| | | |
|---|---|---|
| C07C 319/06 | (2006.01) | |
| C07C 319/24 | (2006.01) | |
| C07C 319/12 | (2006.01) | |
| C07C 321/28 | (2006.01) | |
| C07C 321/26 | (2006.01) | |

(52) U.S. Cl.
CPC .......... *C07C 319/06* (2013.01); *C07C 319/12* (2013.01); *C07C 319/24* (2013.01); *C07C 321/26* (2013.01); *C07C 321/28* (2013.01)

(58) Field of Classification Search
CPC ... C07C 319/12; C07C 319/24; C07C 319/06; C07C 321/28; C07C 321/26
See application file for complete search history.

(56) References Cited

FOREIGN PATENT DOCUMENTS

| | | |
|---|---|---|
| CN | 107286057 A | 10/2017 |
| DE | 961042 C3 | 3/1957 |
| DE | 1139113 B2 | 11/1962 |
| DE | 2119518 A | 10/1972 |
| EP | 0006990 A1 | 1/1980 |
| JP | 2002-260730 A | 9/2002 |
| JP | 2016-084346 A | 5/2016 |
| WO | WO 2015/122396 A1 | 8/2015 |

OTHER PUBLICATIONS

Marrs, JMPR, Methiocarb, 1998, pp. 1-21, Recovered from http://www.inchem.org/documents/jmpr/jmpmono/v098pr11.htm on Jul. 14, 2020. (Year: 1998).*
CAS Registry No. 36552-39-3, Database Registry [online] Nov. 16, 1984, retrieval date Apr. 17, 2019, retrieved from : STN.
CAS Registry No. 36552-40-6, Database Registry [online] Nov. 16, 1984, retrieval date Apr. 17, 2019, retrieved from : STN.
CAS Registry No. 36552-41-7, Database Registry [online] Nov. 16, 1984, retrieval date Apr. 17, 2019, retrieved from : STN.
CAS Registry No. 36552-43-9, Database Registry [online] Nov. 16, 1984, retrieval date Apr. 17, 2019, retrieved from : STN.
John et al., "Palladium Catalyzed C—H Functionalization of 0-Arylcarbamates: Selective ortho-Bromination Using NBS," The Journal of Organic Chemistry, 2012, 77:5600-5605.
Sun et al., "PD(II) catalyzed ortho C—H iodination of phenylcarbamates at room temperature using cyclic hypervalent iodine reagents," Chemical Communications, 2015, 51:10014-10017.
Sun et al., "Room-temperature PD-catalyzed C—H chlorination by weak coordination: one-pot synthesis of 2-chlorophenols with excellent regioselectivity," Chemical Communications, 2014, 50:1262-1264.

* cited by examiner

*Primary Examiner* — Paul A Zucker
(74) *Attorney, Agent, or Firm* — Foley & Lardner LLP

(57) ABSTRACT

A production method in which a mercaptophenol compound is obtained using an industrially preferred sulfur atom introduction reaction, and intermediate compounds of the mercaptophenol compound are provided. A method for producing a mercaptophenol compound in which a phenyl carbamate compound is produced using a phenol compound as a raw material, and then a sulfur atom is regioselectively introduced by a reaction with sulfur monochloride, and a phenyl mercaptocarbamate compound is produced as an intermediate.

16 Claims, No Drawings

METHOD FOR PRODUCING MERCAPTOPHENOL COMPOUND AND INTERMEDIATE OF SAID COMPOUND

CROSS-REFERENCE TO RELATED APPLICATIONS

This application is the U.S. National Stage of PCT/JP2019/006674, filed Feb. 22, 2019, which claims priority to JP 2018-033523, filed Feb. 27, 2018.

TECHNICAL FIELD

The present invention relates to a method for producing a mercaptophenol compound useful as an intermediate for the synthesis of an agrochemical compound, and particularly to a method for producing a mercaptophenol compound in which a phenyl carbamate compound is produced using a phenol compound as a raw material, and then a sulfur atom is position-selectively introduced by a reaction with sulfur monochloride, and a phenyl mercaptocarbamate compound is produced as an intermediate.

BACKGROUND ART

Mercaptophenol compounds are useful as medicinal and agrochemical compounds and intermediates for their synthesis. For example, pest control agents disclosed in Patent Literature 1, Patent Literature 2, and Patent Literature 3 have a trifluoroethylsulfinyl group on a benzene ring and an alkoxy side chain at the meta position, and it is considered that these common structures are important in the expression of pest control activity.

In the methods for producing mercaptophenol compounds described in Patent Literatures 2 and 3, first, 2-fluoro-4-methylphenol that is a raw material is converted into a phenyl acetate compound or a phenylethyl carbonate compound, and then a chlorosulfonylation reaction is performed for the introduction of a sulfur atom. Then, the reduction of the chlorosulfonyl group is performed using phosphorus, followed by a hydrolysis reaction to produce the target mercaptophenol compound ("Synthesis Example 3" in Patent Literature 2 and "Reference Synthesis Examples 2 and 12" in Patent Literature 3). In addition, also in Non Patent Literatures 1 and 2, the same production routes are described.

In the method for producing a mercaptophenol compound described in Patent Literature 4, first, 2,4-dimethylphenol that is a raw material is converted into a phenyl methanesulfonate compound, and then a chlorosulfonylation reaction is performed for the introduction of a sulfur atom. Then, the reduction of the chlorosulfonyl group is performed using tin, followed by a hydrolysis reaction to produce the target mercaptophenol compound ("Reference Example 2" in this literature).

In the methods for producing mercaptophenol compounds described in Patent Literatures 2, 3, and 4, the chlorosulfonylation reaction is adopted for the introduction of a sulfur atom. The chlorosulfonylation reaction is useful on a laboratory scale as a method for introducing a sulfur atom at the meta position of a phenol. However, a strongly acidic reagent such as fuming sulfuric acid, thionyl chloride, or chlorosulfonic acid is used in a large amount, and therefore the corrosion of a reaction tank, the treatment of a large amount of acidic wastewater, and the like are problems, and therefore improvement has been desired in production on an industrial scale.

On the other hand, sulfur-containing organic compounds generally often have a characteristic offensive odor, and the control of this offensive odor also needs to be considered in production on an industrial scale. In addition to such circumstances, for medicinal and agrochemical compounds and intermediates for their synthesis, it is required to produce high quality target compounds in terms of activity and safety and stability. When an intermediate compound obtained in a production process is a liquid, there is only the choice of distillation for a method for isolating the compound and/or a method for purifying the compound, and when the distillation of a sulfur-containing organic compound is performed on an industrial scale, special equipment and a complicated operation for preventing the diffusion of an offensive odor into the surroundings are necessary. When an intermediate compound obtained in a production process is a solid, the choices of filtration and/or recrystallization are provided as an isolation method and/or a purification method, and the quality improvement and storage stability of the intermediate compound are also expected.

CITATION LIST

Patent Literature

[Patent Literature 1] International Publication No. WO 2013/157229
[Patent Literature 2] International Publication No. WO 2013/111864
[Patent Literature 3] International Publication No. WO 2015/025826
[Patent Literature 4] International Publication No. WO 2015/122396

Non Patent Literature

[Non Patent Literature 1] "Preparation of m-hydroxyphenylsulfonic acids and m-hydroxythiophenol" (Wessely, F.; Silhan, W.; Polansky, O. E.) Monatshefte fuer Chemie, vol. 99, p. 2048-2058 (1968)
[Non Patent Literature 2] "Action of thiols and sulfinic acids on quinol acetates. II" (Wessely, F.; Swoboda, J.; Schmidt, G.) Monatshefte fuer Chemie, vol. 91, p. 57-78 (1960)

SUMMARY OF INVENTION

Technical Problem

It is an object of the present invention to provide a method for producing a mercaptophenol compound using an industrially preferred sulfur atom introduction reaction without using a chlorosulfonylation reaction for the introduction of a sulfur atom, and an intermediate compound of the mercaptophenol compound.

It is another object of the present invention to provide an intermediate compound having high crystallinity for which the choices of filtration and/or recrystallization are provided as an isolation method and/or a purification method.

Solution to Problem

In view of the circumstances as described above, the present inventor has repeatedly diligently studied a method for producing a mercaptophenol compound, and as a result, unexpectedly, it has been found that the crystallinity of a phenyl carbamate compound is high. Further, it has been found that a sulfur atom is position-selectively introduced by the reaction of a phenyl carbamate compound with sulfur monochloride, and a method for producing a high quality mercaptophenol compound in which a phenyl mercaptocarbamate compound is produced as an intermediate has been found, and the present invention has been completed.

Specifically, the present invention solves the above problems by providing inventions according to the following [1] to [112] items:

[1] A 5-mercaptophenyl carbamate compound represented by formula (1):

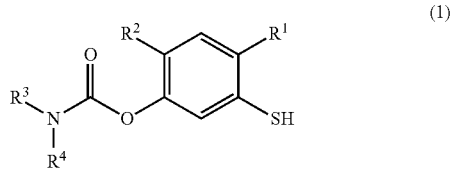

wherein $R^1$ and $R^2$ each independently represent a $C_1$-$C_4$ alkyl group or a halogen atom,
$R^3$ and $R^4$ each independently represent a hydrogen atom, a $C_1$-$C_6$ alkyl group that may be substituted with one or two or more identical or different halogen atoms, a $C_2$-$C_6$ alkenyl group that may be substituted with one or two or more identical or different halogen atoms, a $C_3$-$C_6$ cycloalkyl group that may be substituted with one or two or more identical or different halogen atoms, a $C_1$-$C_6$ alkoxy group that may be substituted with one or two or more identical or different halogen atoms, a $C_6$-$C_{10}$ aryl group that may be substituted with one or two or more identical or different substituents A, or a $C_6$-$C_{10}$ aryl $C_1$-$C_4$ alkyl group that may be substituted with one or two or more identical or different substituents A,
or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B,
the substituent A represents a $C_1$-$C_4$ alkyl group or a halogen atom, and
the substituent B represents a $C_1$-$C_4$ alkyl group, a halogen atom, or an oxo group.

[2] The compound according to [1], wherein in the formula (1),
$R^1$ and $R^2$ each independently represent a $C_1$-$C_4$ alkyl group or a halogen atom,
$R^3$ and $R^4$ each independently represent a hydrogen atom, a $C_1$-$C_6$ alkyl group that may be substituted with one or two or more identical or different halogen atoms, a phenyl group that may be substituted with one or two or more identical or different substituents A, or a benzyl group that may be substituted with one or two or more identical or different substituents A,
or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B,
the substituent A represents a $C_1$-$C_4$ alkyl group or a halogen atom, and
the substituent B represents a $C_1$-$C_4$ alkyl group, a halogen atom, or an oxo group.

[3] The compound according to [1], wherein in the formula (1),
$R^1$ and $R^2$ each independently represent a methyl group, a fluorine atom, or a chlorine atom, and
$R^3$ and $R^4$ each independently represent a hydrogen atom, a methyl group, an ethyl group, a propyl group, an isopropyl group, a phenyl group, or a benzyl group,
or $R^3$ and $R^4$ may together form a 4- to 8-membered ring by forming a divalent group selected from the group consisting of a propylene group, a butylene group, a pentylene group, a hexylene group, a heptylene group, an -(ethylene)-O-(ethylene)- group, and an -(ethylene)-N-(ethylene)- group.

[4] The compound according to [1], wherein in the formula (1),
$R^1$ and $R^2$ each independently represent a methyl group, a fluorine atom, or a chlorine atom, and
$R^3$ and $R^4$ each independently represent a methyl group, an ethyl group, a propyl group, or an isopropyl group.

[5] The compound according to [1], wherein in the formula (1),
$R^1$ represents a methyl group or a chlorine atom,
$R^2$ represents a methyl group or a fluorine atom, and
$R^3$ and $R^4$ represent a methyl group.

[6] The compound according to [1], wherein in the formula (1),
$R^1$ represents a chlorine atom,
$R^2$ represents a fluorine atom, and
$R^3$ and $R^4$ each independently represent a methyl group, an ethyl group, a propyl group, or an isopropyl group.

[7] The compound according to [1], wherein in the formula (1),
$R^1$ represents a chlorine atom,
$R^2$ represents a fluorine atom, and
$R^3$ and $R^4$ represent a methyl group.

[8] A polysulfide compound represented by formula (2):

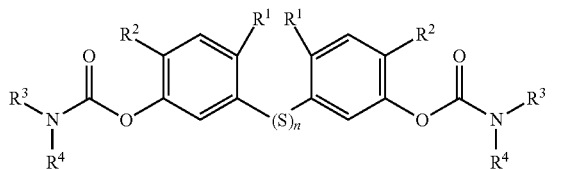

wherein $R^1$ and $R^2$ each independently represent a $C_1$-$C_4$ alkyl group or a halogen atom,
$R^3$ and $R^4$ each independently represent a hydrogen atom, a $C_1$-$C_6$ alkyl group that may be substituted with one or two or more identical or different halogen atoms, a $C_2$-$C_6$ alkenyl group that may be substituted with one or two or more identical or different halogen atoms, a $C_3$-$C_6$ cycloalkyl group that may be substituted with one or two or more identical or different halogen atoms, a $C_1$-$C_6$ alkoxy group that may be substituted with one or two or more identical or different halogen atoms, a $C_6$-$C_{10}$ aryl group that may be substituted with one or two or more identical or different substituents A, or a $C_6$-$C_{10}$ aryl $C_1$-$C_4$ alkyl group that may be substituted with one or two or more identical or different substituents A, or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B, the substituent A represents a $C_1$-$C_4$ alkyl group or a halogen atom, the substituent B represents a $C_1$-$C_4$ alkyl group, a halogen atom, or an oxo group, and n represents an integer of 2 or more, or a mixture thereof.

[9] The compound according to [8], wherein in the formula (2), $R^1$ and $R^2$ each independently represent a $C_1$-$C_4$ alkyl group or a halogen atom, $R^3$ and $R^4$ each independently represent a hydrogen atom, a $C_1$-$C_6$ alkyl group that may be substituted with one or two or more identical or different halogen atoms, a phenyl group that may be substituted with one or two or more identical or different substituents A, or a benzyl group that may be substituted with one or two or more identical or different substituents A, or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B, the substituent A represents a $C_1$-$C_4$ alkyl group or a halogen atom, the substituent B represents a $C_1$-$C_4$ alkyl group, a halogen atom, or an oxo group, and n represents an integer in the range of 2 to 10.

[10] The compound according to [8], wherein in the formula (2), $R^1$ and $R^2$ each independently represent a methyl group, a fluorine atom, or a chlorine atom, $R^3$ and $R^4$ each independently represent a hydrogen atom, a methyl group, an ethyl group, a propyl group, an isopropyl group, a phenyl group, or a benzyl group, or $R^3$ and $R^4$ may together form a 4- to 8-membered ring by forming a divalent group selected from the group consisting of a propylene group, a butylene group, a pentylene group, a hexylene group, a heptylene group, an -(ethylene)-O-(ethylene)- group, and an -(ethylene)-NH-(ethylene)- group, and n represents an integer in the range of 2 to 8.

[11] The compound according to [8], wherein in the formula (2), $R^1$ and $R^2$ each independently represent a methyl group, a fluorine atom, or a chlorine atom, $R^3$ and $R^4$ each independently represent a methyl group, an ethyl group, a propyl group, or an isopropyl group, and n represents an integer in the range of 2 to 6.

[12] The compound according to [8], wherein in the formula (2), $R^1$ represents a methyl group or a chlorine atom, $R^2$ represents a methyl group or a fluorine atom, $R^3$ and $R^4$ represent a methyl group, and n represents an integer in the range of 2 to 5.

[13] The compound according to [8], wherein in the formula (2), $R^1$ represents a chlorine atom, $R^2$ represents a fluorine atom, $R^3$ and $R^4$ each independently represent a methyl group, an ethyl group, a propyl group, or an isopropyl group, and n represents an integer in the range of 2 to 5.

[14] The compound according to [8], wherein in the formula (2), $R^1$ represents a chlorine atom, $R^2$ represents a fluorine atom, $R^3$ and $R^4$ represent a methyl group, and n represents an integer in the range of 2 to 5.

[15] A phenyl carbamate compound represented by formula (3):

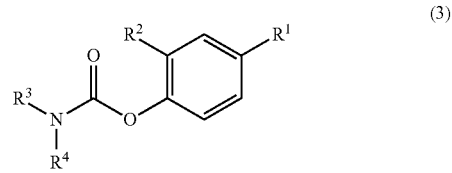

(3)

wherein $R^1$ and $R^2$ each independently represent a $C_1$-$C_4$ alkyl group or a halogen atom, $R^3$ and $R^4$ each independently represent a hydrogen atom, a $C_1$-$C_6$ alkyl group that may be substituted with one or two or more identical or different halogen atoms, a $C_2$-$C_6$ alkenyl group that may be substituted with one or two or more identical or different halogen atoms, a $C_3$-$C_6$ cycloalkyl group that may be substituted with one or two or more identical or different halogen atoms, a $C_1$-$C_6$ alkoxy group that may be substituted with one or two or more identical or different halogen atoms, a $C_6$-$C_{10}$ aryl group that may be substituted with one or two or more identical or different substituents A, or a $C_6$-$C_{10}$ aryl $C_1$-$C_4$ alkyl group that may be substituted with one or two or more identical or different substituents A, or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B, the substituent A represents a $C_1$-$C_4$ alkyl group or a halogen atom, and the substituent B represents a $C_1$-$C_4$ alkyl group, a halogen atom, or an oxo group.

[16] The compound according to [15], wherein in the formula (3), $R^1$ and $R^2$ each independently represent a $C_1$-$C_4$ alkyl group or a halogen atom, $R^3$ and $R^4$ each independently represent a hydrogen atom, a $C_1$-$C_6$ alkyl group that may be substituted with one or two or more identical or different halogen atoms, a phenyl group that may be substituted with one or two or more identical or different substituents A, or a benzyl group that may be substituted with one or two or more identical or different substituents A, or $R^3$ and $R^4$ may together form a 4- to 8-membered ring by forming a divalent group selected from the group consisting of a $C_3$-$C_7$ alkylene group that may be substituted with one or two or more identical or different substituents B, a
—($C_1$-$C_3$ alkylene)-O—($C_1$-$C_3$ alkylene)- group that may be
substituted with one or two or more identical or different
substituents B, and a —($C_1$-$C_3$ alkylene)-NH—($C_1$-$C_3$ alkylene)- group that may be substituted with one or two or more
identical or different substituents B,
the substituent A represents a $C_1$-$C_4$ alkyl group or a halogen atom, and
the substituent B represents a $C_1$-$C_4$ alkyl group, a halogen atom, or an oxo group.

[17] The compound according to [15], wherein in the formula (3),
$R^1$ and $R^2$ each independently represent a methyl group, a fluorine atom, or a chlorine atom, and
$R^3$ and $R^4$ each independently represent a hydrogen atom, a methyl group, an ethyl group, a propyl group, an isopropyl group, a phenyl group, or a benzyl group,
or $R^3$ and $R^4$ may together form a 4- to 8-membered ring by forming a divalent group selected from the group consisting of a propylene group, a butylene group, a pentylene group, a hexylene group, a heptylene group, an -(ethylene)-O-(ethylene)- group, and an -(ethylene)-NH-(ethylene)- group.

[18] The compound according to [15], wherein in the formula (3),
$R^1$ and $R^2$ each independently represent a methyl group, a fluorine atom, or a chlorine atom, and
$R^3$ and $R^4$ each independently represent a methyl group, an ethyl group, a propyl group, or an isopropyl group.

[19] The compound according to [15], wherein in the formula (3),
$R^1$ represents a methyl group or a chlorine atom,
$R^2$ represents a methyl group or a fluorine atom, and
$R^3$ and $R^4$ represent a methyl group.

[20] The compound according to [15], wherein in the formula (3),
$R^1$ represents a chlorine atom,
$R^2$ represents a fluorine atom, and
$R^3$ and $R^4$ each independently represent a methyl group, an ethyl group, a propyl group, or an isopropyl group.

[21] The compound according to [15], wherein in the formula (3),
$R^1$ represents a chlorine atom,
$R^2$ represents a fluorine atom, and
$R^3$ and $R^4$ represent a methyl group.

[22] A method for producing a polysulfide compound represented by formula (2):

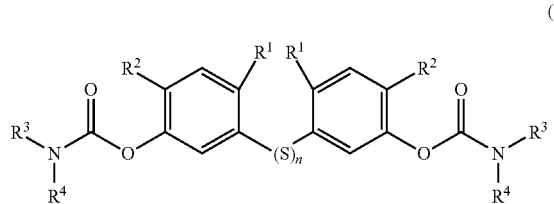

wherein $R^1$ and $R^2$ each independently represent a $C_1$-$C_4$ alkyl group or a halogen atom,
$R^3$ and $R^4$ each independently represent a hydrogen atom, a $C_1$-$C_6$ alkyl group that may be substituted with one or two or more identical or different halogen atoms, a $C_2$-$C_6$ alkenyl group that may be substituted with one or two or more identical or different halogen atoms, a $C_3$-$C_6$ cycloalkyl group that may be substituted with one or two or more identical or different halogen atoms, a $C_1$-$C_6$ alkoxy group that may be substituted with one or two or more identical or different halogen atoms, a $C_6$-$C_{10}$ aryl group that may be substituted with one or two or more identical or different substituents A, or a $C_6$-$C_{10}$ aryl $C_1$-$C_4$ alkyl group that may be substituted with one or two or more identical or different substituents A,
or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B,
the substituent A represents a $C_1$-$C_4$ alkyl group or a halogen atom,
the substituent B represents a $C_1$-$C_4$ alkyl group, a halogen atom, or an oxo group, and
n represents an integer of 2 or more,
or a mixture thereof, comprising the following steps:
(i) a step of reacting a compound represented by formula (5):

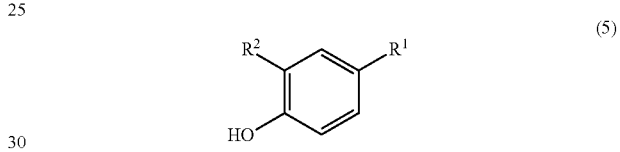

wherein $R^1$ and $R^2$ are as defined above,
with a carbamoyl halide compound represented by formula (a):

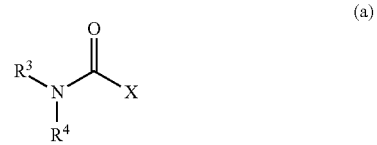

wherein $R^3$ and $R^4$ are as defined above, and X represents a halogen atom,
in the presence of a base to produce a compound represented by formula (3):

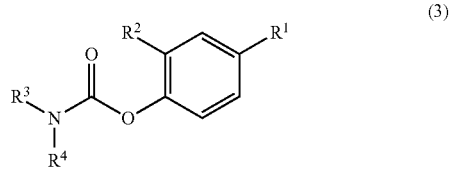

wherein $R^1$, $R^2$, $R^3$, and $R^4$ are as defined above; and
(ii) a step of subjecting the compound represented by the formula (3) to a reaction with a sulfur compound in the presence of an acid to produce the compound represented by the formula (2).

[23] The method according to [22], wherein $R^1$ and $R^2$ each independently represent a $C_1$-$C_4$ alkyl group or a halogen atom,
$R^3$ and $R^4$ each independently represent a hydrogen atom, a $C_1$-$C_6$ alkyl group that may be substituted with one or two or more identical or different halogen atoms, a phenyl group that may be substituted with one or two or more identical or different substituents A, or a benzyl group that may be substituted with one or two or more identical or different substituents A,
or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B,
the substituent A represents a $C_1$-$C_4$ alkyl group or a halogen atom,
the substituent B represents a $C_1$-$C_4$ alkyl group, a halogen atom, or an oxo group,
n represents an integer in the range of 2 to 10, and
X represents a halogen atom.

[24] The method according to [22], wherein $R^1$ and $R^2$ each independently represent a methyl group, a fluorine atom, or a chlorine atom,
$R^3$ and $R^4$ each independently represent a hydrogen atom, a methyl group, an ethyl group, a propyl group, an isopropyl group, a phenyl group, or a benzyl group,
or $R^3$ and $R^4$ may together form a 4- to 8-membered ring by forming a divalent group selected from the group consisting of a propylene group, a butylene group, a pentylene group, a hexylene group, a heptylene group, an -(ethylene)-O-(ethylene)- group, and an -(ethylene)-NH-(ethylene)- group,
n represents an integer in the range of 2 to 8, and
X represents a halogen atom.

[25] The method according to [22], wherein $R^1$ and $R^2$ each independently represent a methyl group, a fluorine atom, or a chlorine atom,
$R^3$ and $R^4$ each independently represent a methyl group, an ethyl group, a propyl group, or an isopropyl group,
n represents an integer in the range of 2 to 6, and
X represents a chlorine atom.

[26] The method according to [22], wherein $R^1$ represents a methyl group or a chlorine atom,
$R^2$ represents a methyl group or a fluorine atom,
$R^3$ and $R^4$ represent a methyl group,
n represents an integer in the range of 2 to 5, and
X represents a chlorine atom.

[27] The method according to [22], wherein $R^1$ represents a chlorine atom,
$R^2$ represents a fluorine atom,
$R^3$ and $R^4$ each independently represent a methyl group, an ethyl group, a propyl group, or an isopropyl group,
n represents an integer in the range of 2 to 5, and
X represents a chlorine atom.

[28] The method according to [22], wherein $R^1$ represents a chlorine atom,
$R^2$ represents a fluorine atom,
$R^3$ and $R^4$ represent a methyl group,
n represents an integer in the range of 2 to 5, and
X represents a chlorine atom.

[29] The method according to any one of [22] to [28], wherein the base used in the step (i) is triethylamine, diisopropylethylamine, 1,8-diazabicyclo[5.4.0]-7-undec-7-ene (DBU), 1,4-diazabicyclo[2.2.2]octane (DABCO), N,N-dimethylaniline, N,N-diethylaniline, pyridine, 4-(dimethylamino)-pyridine, 2,6-lutidine, or a mixture thereof.

[30] The method according to any one of [22] to [28], wherein the base used in the step (i) is triethylamine, diisopropylethylamine, N,N-dimethylaniline, N,N-diethylaniline, pyridine, 4-(dimethylamino)-pyridine, 2,6-lutidine, or a mixture thereof.

[31] The method according to any one of [22] to [28], wherein the base used in the step (i) is triethylamine, 4-(dimethylamino)-pyridine, or a mixture thereof.

[32] The method according to any one of [22] to [31], wherein the base in the range of 0.03 equivalents or more and 3.0 equivalents or less relative to 1.0 mol of the compound of the formula (5) is used.

[33] The method according to any one of [22] to [31], wherein the base in the range of 0.05 equivalents or more and 2.0 equivalents or less relative to 1.0 mol of the compound of the formula (5) is used.

[34] The method according to any one of [22] to [33], wherein the acid used in the step (ii) is a Lewis acid.

[35] The method according to any one of [22] to [33], wherein the acid used in the step (ii) is aluminum chloride, aluminum bromide, iron(III) chloride, zinc(II) chloride, boron trifluoride, or a mixture thereof.

[36] The method according to any one of [22] to [33], wherein the acid used in the step (ii) is aluminum chloride.

[37] The method according to any one of [22] to [36], wherein the acid in the range of 0.03 equivalents or more and 3.0 equivalents or less relative to 1.0 mol of the compound of the formula (3) is used.

[38] The method according to any one of [22] to [36], wherein the acid in the range of 0.05 equivalents or more and 2.0 equivalents or less relative to 1.0 mol of the compound of the formula (3) is used.

[39] The method according to any one of [22] to [38], wherein the sulfur compound used in the step (ii) is a sulfur chloride compound.

[40] The method according to any one of [22] to [38], wherein the sulfur compound used in the step (ii) is sulfur monochloride.

[41] The method according to any one of [22] to [40], wherein the sulfur compound in the range of 1.1 equivalents or more and 3.0 equivalents or less relative to 1.0 mol of the compound of the formula (3) is used.

[42] The method according to any one of [22] to [40], wherein the sulfur compound in the range of 1.2 equivalents or more and 2.0 equivalents or less relative to 1.0 mol of the compound of the formula (3) is used.

[43] A method for producing a 5-mercaptophenyl carbamate compound represented by formula (1):

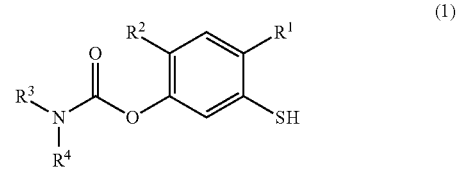

(1)

wherein $R^1$ and $R^2$ each independently represent a $C_1$-$C_4$ alkyl group or a halogen atom,
$R^3$ and $R^4$ each independently represent a hydrogen atom, a $C_1$-$C_6$ alkyl group that may be substituted with one or two or more identical or different halogen atoms, a $C_2$-$C_6$ alkenyl group that may be substituted with one or two or more identical or different halogen atoms, a $C_3$-$C_6$ cycloalkyl group that may be substituted with one or two or more identical or different halogen atoms, a $C_1$-$C_6$ alkoxy group that may be substituted with one or two or more identical or different halogen atoms, a $C_6$-$C_{10}$ aryl group that may be substituted with one or two or more identical or different substituents A, or a $C_6$-$C_{10}$ aryl $C_1$-$C_4$ alkyl group that may be substituted with one or two or more identical or different substituents A, or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B, the substituent A represents a $C_1$-$C_4$ alkyl group or a halogen atom, and the substituent B represents a $C_1$-$C_4$ alkyl group, a halogen atom, or an oxo group, comprising the following steps:

(i) a step of reacting a compound represented by formula (5):

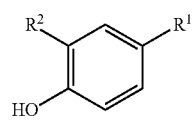

(5)

wherein $R^1$ and $R^2$ are as defined above, with a carbamoyl halide compound represented by formula (a):

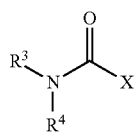

(a)

wherein $R^3$ and $R^4$ are as defined above, and X represents a halogen atom, in the presence of a base to produce a compound represented by formula (3):

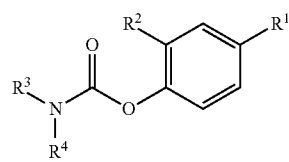

(3)

wherein $R^1$, $R^2$, $R^3$, and $R^4$ are as defined above;

(ii) a step of subjecting the compound represented by the formula (3) to a reaction with a sulfur compound in the presence of an acid to produce a polysulfide compound represented by formula (2):

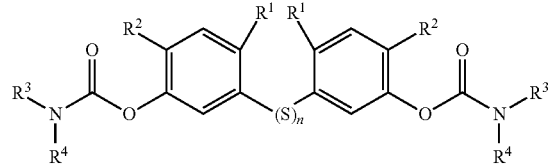

(2)

wherein $R^1$, $R^2$, $R^3$, and $R^4$ are as defined above, and n represents an integer of 2 or more, or a mixture thereof; and (iii) a step of producing the compound represented by the formula (1) from the compound represented by the formula (2).

[44] The method according to [43], wherein $R^1$ and $R^2$ each independently represent a $C_1$-$C_4$ alkyl group or a halogen atom, $R^3$ and $R^4$ each independently represent a hydrogen atom, a $C_1$-$C_6$ alkyl group that may be substituted with one or two or more identical or different halogen atoms, a phenyl group that may be substituted with one or two or more identical or different substituents A, or a benzyl group that may be substituted with one or two or more identical or different substituents A, or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B, the substituent A represents a $C_1$-$C_4$ alkyl group or a halogen atom, the substituent B represents a $C_1$-$C_4$ alkyl group, a halogen atom, or an oxo group, n represents an integer in the range of 2 to 10, and X represents a halogen atom.

[45] The method according to [43], wherein $R^1$ and $R^2$ each independently represent a methyl group, a fluorine atom, or a chlorine atom, $R^3$ and $R^4$ each independently represent a hydrogen atom, a methyl group, an ethyl group, a propyl group, an isopropyl group, a phenyl group, or a benzyl group, or $R^3$ and $R^4$ may together form a 4- to 8-membered ring by forming a divalent group selected from the group consisting of a propylene group, a butylene group, a pentylene group, a hexylene group, a heptylene group, an -(ethylene)-O-(ethylene)- group, and an -(ethylene)-NH-(ethylene)- group, n represents an integer in the range of 2 to 8, and X represents a halogen atom.

[46] The method according to [43], wherein $R^1$ and $R^2$ each independently represent a methyl group, a fluorine atom, or a chlorine atom, $R^3$ and $R^4$ each independently represent a methyl group, an ethyl group, a propyl group, or an isopropyl group, n represents an integer in the range of 2 to 6, and X represents a chlorine atom.

[47] The method according to [43], wherein $R^1$ represents a methyl group or a chlorine atom, $R^2$ represents a methyl group or a fluorine atom, $R^3$ and $R^4$ represent a methyl group, n represents an integer in the range of 2 to 5, and
X represents a chlorine atom.

[48] The method according to [43], wherein $R^1$ represents a chlorine atom,
$R^2$ represents a fluorine atom,
$R^3$ and $R^4$ each independently represent a methyl group, an ethyl group, a propyl group, or an isopropyl group,
n represents an integer in the range of 2 to 5, and
X represents a chlorine atom.

[49] The method according to [43], wherein $R^1$ represents a chlorine atom,
$R^2$ represents a fluorine atom,
$R^3$ and $R^4$ represent a methyl group,
n represents an integer in the range of 2 to 5, and
X represents a chlorine atom.

[50] The method according to any one of [43] to [49], wherein the base used in the step (i) is triethylamine, diisopropylethylamine, 1,8-diazabicyclo[5.4.0]-7-undec-7-ene (DBU), 1,4-diazabicyclo[2.2.2]octane (DABCO), N,N-dimethylaniline, N,N-diethylaniline, pyridine, 4-(dimethyl-amino)-pyridine, 2,6-lutidine, or a mixture thereof.

[51] The method according to any one of [43] to [49], wherein the base used in the step (i) is triethylamine, diisopropylethylamine, N,N-dimethylaniline, N,N-diethyl-aniline, pyridine, 4-(dimethylamino)-pyridine, 2,6-lutidine, or a mixture thereof.

[52] The method according to any one of [43] to [49], wherein the base used in the step (i) is triethylamine, 4-(dimethylamino)-pyridine, or a mixture thereof.

[53] The method according to any one of [43] to [52], wherein the base in the range of 0.03 equivalents or more and 3.0 equivalents or less relative to 1.0 mol of the compound of the formula (5) is used.

[54] The method according to any one of [43] to [52], wherein the base in the range of 0.05 equivalents or more and 2.0 equivalents or less relative to 1.0 mol of the compound of the formula (5) is used.

[55] The method according to any one of [43] to [54], wherein the acid used in the step (ii) is a Lewis acid.

[56] The method according to any one of [43] to [54], wherein the acid used in the step (ii) is aluminum chloride, aluminum bromide, iron(III) chloride, zinc(II) chloride, boron trifluoride, or a mixture thereof.

[57] The method according to any one of [43] to [54], wherein the acid used in the step (ii) is aluminum chloride.

[58] The method according to any one of [43] to [57], wherein the acid in the range of 0.03 equivalents or more and 3.0 equivalents or less relative to 1.0 mol of the compound of the formula (3) is used.

[59] The method according to any one of [43] to [57], wherein the acid in the range of 0.05 equivalents or more and 2.0 equivalents or less relative to 1.0 mol of the compound of the formula (3) is used.

[60] The method according to any one of [43] to [59], wherein the sulfur compound used in the step (ii) is a sulfur chloride compound.

[61] The method according to any one of [43] to [59], wherein the sulfur compound used in the step (ii) is sulfur monochloride.

[62] The method according to any one of [43] to [61], wherein the sulfur compound in the range of 1.1 equivalents or more and 3.0 equivalents or less relative to 1.0 mol of the compound of the formula (3) is used.

[63] The method according to any one of [43] to [61], wherein the sulfur compound in the range of 1.2 equivalents or more and 2.0 equivalents or less relative to 1.0 mol of the compound of the formula (3) is used.

[64] The method according to any one of [43] to [63], wherein the step (iii) is performed in the presence of a reducing agent or a base.

[65] The method according to any one of [43] to [63], wherein the step (iii) is performed in the presence of a reducing agent and a base.

[66] The method according to any one of [43] to [65], wherein the reducing agent used in the step (iii) is a metal, a borohydride reagent, an alkali metal sulfide, an alkali metal hydroxymethanesulfinate, or a mixture thereof.

[67] The method according to any one of [43] to [65], wherein the reducing agent used in the step (iii) is an alkali metal sulfide, an alkali metal hydroxymethanesulfinate, or a mixture thereof.

[68] The method according to any one of [43] to [65], wherein the reducing agent used in the step (iii) is an alkali metal hydroxymethanesulfinate.

[69] The method according to any one of [43] to [65], wherein the reducing agent used in the step (iii) is sodium hydroxymethanesulfinate.

[70] The method according to any one of [43] to [69], wherein the reducing agent in the range of 0.05 equivalents or more and 5.0 equivalents or less relative to 1.0 mol of the compound of the formula (2) is used.

[71] The method according to any one of [43] to [69], wherein the reducing agent in the range of 0.1 equivalents or more and 4.0 equivalents or less relative to 1.0 mol of the compound of the formula (2) is used.

[72] The method according to any one of [43] to [71], wherein the base used in the step (iii) is an alkali metal carbonate, an alkali metal hydrogen carbonate, or a mixture thereof.

[73] The method according to any one of [43] to [71], wherein the base used in the step (iii) is an alkali metal carbonate.

[74] The method according to any one of [43] to [71], wherein the base used in the step (iii) is sodium carbonate, potassium carbonate, sodium hydrogen carbonate, potassium hydrogen carbonate, or a mixture thereof.

[75] The method according to any one of [43] to [71], wherein the base used in the step (iii) is sodium carbonate.

[76] The method according to any one of [43] to [75], wherein the base in the range of 0.03 equivalents or more and 4.0 equivalents or less relative to 1.0 mol of the compound of the formula (2) is used.

[77] The method according to any one of [43] to [75], wherein the base in the range of 0.05 equivalents or more and 3.0 equivalents or less relative to 1.0 mol of the compound of the formula (2) is used.

[78] A method for producing a mercaptophenol compound represented by formula (4):

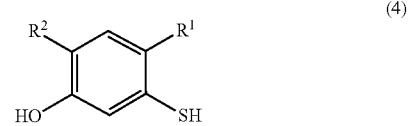

(4)

wherein $R^1$ and $R^2$ each independently represent a $C_1$-$C_4$ alkyl group or a halogen atom, comprising the following steps:
(i) a step of reacting a compound represented by formula (5):

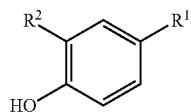 (5)

wherein $R^1$ and $R^2$ are as defined above,
with a carbamoyl halide compound represented by formula (a):

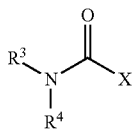 (a)

wherein $R^3$ and $R^4$ each independently represent a hydrogen atom, a $C_1$-$C_6$ alkyl group that may be substituted with one or two or more identical or different halogen atoms, a $C_2$-$C_6$ alkenyl group that may be substituted with one or two or more identical or different halogen atoms, a $C_3$-$C_6$ cycloalkyl group that may be substituted with one or two or more identical or different halogen atoms, a $C_1$-$C_6$ alkoxy group that may be substituted with one or two or more identical or different halogen atoms, a $C_6$-$C_{10}$ aryl group that may be substituted with one or two or more identical or different substituents A, or a $C_6$-$C_{10}$ aryl $C_1$-$C_4$ alkyl group that may be substituted with one or two or more identical or different substituents A,
or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B,
the substituent A represents a $C_1$-$C_4$ alkyl group or a halogen atom,
the substituent B represents a $C_1$-$C_4$ alkyl group, a halogen atom, or an oxo group, and
X represents a halogen atom,
in the presence of a base to produce a compound represented by formula (3):

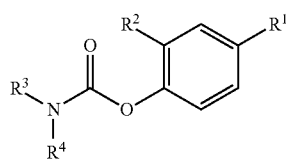 (3)

wherein $R^1$, $R^2$, $R^3$, and $R^4$ are as defined above;
(ii) a step of subjecting the compound represented by the formula (3) to a reaction with a sulfur compound in the presence of an acid to produce a compound represented by formula (2):

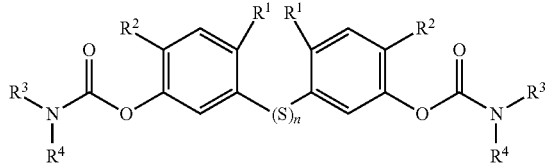 (2)

wherein $R^1$, $R^2$, $R^3$, and $R^4$ are as defined above, and n represents an integer of 2 or more;
(iii) a step of producing a compound represented by formula (1):

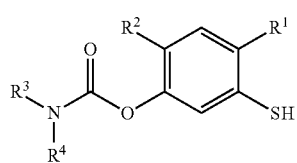 (1)

wherein $R^1$, $R^2$, $R^3$, and $R^4$ are as defined above,
from the compound represented by the formula (2); and
(iv) a step of producing the compound represented by the formula (4) from the compound represented by the formula (1).

[79] The method according to [78], wherein $R^1$ and $R^2$ each independently represent a $C_1$-$C_4$ alkyl group or a halogen atom,
$R^3$ and $R^4$ each independently represent a hydrogen atom, a $C_1$-$C_6$ alkyl group that may be substituted with one or two or more identical or different halogen atoms, a phenyl group that may be substituted with one or two or more identical or different substituents A, or a benzyl group that may be substituted with one or two or more identical or different substituents A,
or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B,
the substituent A represents a $C_1$-$C_4$ alkyl group or a halogen atom,
the substituent B represents a $C_1$-$C_4$ alkyl group, a halogen atom, or an oxo group,
n represents an integer in the range of 2 to 10, and
X represents a halogen atom.
[80] The method according to [78], wherein $R^1$ and $R^2$ each independently represent a methyl group, a fluorine atom, or a chlorine atom,
$R^3$ and $R^4$ each independently represent a hydrogen atom, a methyl group, an ethyl group, a propyl group, an isopropyl group, a phenyl group, or a benzyl group,
or $R^3$ and $R^4$ may together form a 4- to 8-membered ring by forming a divalent group selected from the group consisting of a propylene group, a butylene group, a pentylene group, a hexylene group, a heptylene group, a -(ethylene)-O-(ethylene)- group, and an -(ethylene)-NH-(ethylene)- group,
n represents an integer in the range of 2 to 8, and X represents a halogen atom.

[81] The method according to [78], wherein $R^1$ and $R^2$ each independently represent a methyl group, a fluorine atom, or a chlorine atom,
$R^3$ and $R^4$ each independently represent a methyl group, an ethyl group, a propyl group, or an isopropyl group,
n represents an integer in the range of 2 to 6, and
X represents a chlorine atom.

[82] The method according to [78], wherein $R^1$ represents a methyl group or a chlorine atom,
$R^2$ represents a methyl group or a fluorine atom,
$R^3$ and $R^4$ represent a methyl group,
n represents an integer in the range of 2 to 5, and
X represents a chlorine atom.

[83] The method according to [78], wherein $R^1$ represents a chlorine atom,
$R^2$ represents a fluorine atom,
$R^3$ and $R^4$ each independently represent a methyl group, an ethyl group, a propyl group, or an isopropyl group,
n represents an integer in the range of 2 to 5, and
X represents a chlorine atom.

[84] The method according to [78], wherein $R^1$ represents a chlorine atom,
$R^2$ represents a fluorine atom,
$R^3$ and $R^4$ represent a methyl group,
n represents an integer in the range of 2 to 5, and
X represents a chlorine atom.

[85] The method according to any one of [78] to [84], wherein the base used in the step (i) is triethylamine, diisopropylethylamine, 1,8-diazabicyclo[5.4.0]-7-undec-7-ene (DBU), 1,4-diazabicyclo[2.2.2]octane (DABCO), N,N-dimethylaniline, N,N-diethylaniline, pyridine, 4-(dimethylamino)-pyridine, 2,6-lutidine, or a mixture thereof.

[86] The method according to any one of [78] to [84], wherein the base used in the step (i) is triethylamine, diisopropylethylamine, N,N-dimethylaniline, N,N-diethylaniline, pyridine, 4-(dimethylamino)-pyridine, 2,6-lutidine, or a mixture thereof.

[87] The method according to any one of [78] to [84], wherein the base used in the step (i) is triethylamine, 4-(dimethylamino)-pyridine, or a mixture thereof.

[88] The method according to any one of [78] to [87], wherein the base in the range of 0.03 equivalents or more and 3.0 equivalents or less relative to 1.0 mol of the compound of the formula (5) is used.

[89] The method according to any one of [78] to [87], wherein the base in the range of 0.05 equivalents or more and 2.0 equivalents or less relative to 1.0 mol of the compound of the formula (5) is used.

[90] The method according to any one of [78] to [89], wherein the acid used in the step (ii) is a Lewis acid.

[91] The method according to any one of [78] to [89], wherein the acid used in the step (ii) is aluminum chloride, aluminum bromide, iron(III) chloride, zinc(II) chloride, boron trifluoride, or a mixture thereof.

[92] The method according to any one of [78] to [89], wherein the acid used in the step (ii) is aluminum chloride.

[93] The method according to any one of [78] to [92], wherein the acid in the range of 0.03 equivalents or more and 3.0 equivalents or less relative to 1.0 mol of the compound of the formula (3) is used.

[94] The method according to any one of [78] to [92], wherein the acid in the range of 0.05 equivalents or more and 2.0 equivalents or less relative to 1.0 mol of the compound of the formula (3) is used.

[95] The method according to any one of [78] to [94], wherein the sulfur compound used in the step (ii) is a sulfur chloride compound.

[96] The method according to any one of [78] to [94], wherein the sulfur compound used in the step (ii) is sulfur monochloride.

[97] The method according to any one of [78] to [96], wherein the sulfur compound in the range of 1.1 equivalents or more and 3.0 equivalents or less relative to 1.0 mol of the compound of the formula (3) is used.

[98] The method according to any one of [78] to [96], wherein the sulfur compound in the range of 1.2 equivalents or more and 2.0 equivalents or less relative to 1.0 mol of the compound of the formula (3) is used.

[99] The method according to any one of [78] to [98], wherein the step (iii) is performed in the presence of a reducing agent or a base.

[100] The method according to any one of [78] to [98], wherein the step (iii) is performed in the presence of a reducing agent and a base.

[101] The method according to any one of [78] to [100], wherein the reducing agent used in the step (iii) is a metal, a borohydride reagent, an alkali metal sulfide, an alkali metal hydroxymethanesulfinate, or a mixture thereof.

[102] The method according to any one of [78] to [100], wherein the reducing agent used in the step (iii) is an alkali metal sulfide, an alkali metal hydroxymethanesulfinate, or a mixture thereof.

[103] The method according to any one of [78] to [100], wherein the reducing agent used in the step (iii) is an alkali metal hydroxymethanesulfinate.

[104] The method according to any one of [78] to [100], wherein the reducing agent used in the step (iii) is sodium hydroxymethanesulfinate.

[105] The method according to any one of [78] to [104], wherein the reducing agent in the range of 0.05 equivalents or more and 5.0 equivalents or less relative to 1.0 mol of the compound of the formula (2) is used.

[106] The method according to any one of [78] to [104], wherein the reducing agent in the range of 0.1 equivalents or more and 4.0 equivalents or less relative to 1.0 mol of the compound of the formula (2) is used.

[107] The method according to any one of [78] to [106], wherein the base used in the step (iii) is an alkali metal carbonate, an alkali metal hydrogen carbonate, or a mixture thereof.

[108] The method according to any one of [78] to [106], wherein the base used in the step (iii) is an alkali metal carbonate.

[109] The method according to any one of [78] to [106], wherein the base used in the step (iii) is sodium carbonate, potassium carbonate, sodium hydrogen carbonate, potassium hydrogen carbonate, or a mixture thereof.

[110] The method according to any one of [78] to [106], wherein the base used in the step (iii) is sodium carbonate.

[111] The method according to any one of [78] to [110], wherein the base in the range of 0.03 equivalents or more and 4.0 equivalents or less relative to 1.0 mol of the compound of the formula (2) is used.

[112] The method according to any one of [78] to [110], wherein the base in the range of 0.05 equivalents or more and 3.0 equivalents or less relative to 1.0 mol of the compound of the formula (2) is used.

Effects of the Invention

According to the present invention, a novel method for producing a mercaptophenol compound useful as an intermediate for the synthesis of an agrochemical compound is provided.

According to the present invention, a production method in which a mercaptophenol compound is obtained using an industrially preferred sulfur atom introduction reaction without using a chlorosulfonylation reaction for the introduction of a sulfur atom, and intermediate compounds of the mercaptophenol compound are provided.

In addition, according to the present invention, an intermediate compound having high crystallinity that provides the choices of filtration and/or recrystallization as an isolation method and/or a purification method is provided.

EMBODIMENTS FOR CARRYING OUT THE INVENTION

1. Symbols and terms described herein will be described.

A halogen atom is a fluorine atom, a chlorine atom, a bromine atom, or an iodine atom.

An expression in element symbols and subscript numbers such as $C_1$-$C_3$ indicates that the number of elements of the group expressed following the expression is in the range indicated by the subscript numbers. For example, the expression $C_1$-$C_3$ indicates that the number of carbon atoms is 1 to 3, the expression $C_1$-$C_6$ indicates that the number of carbon atoms is 1 to 6, and the expression $C_1$-$C_{12}$ indicates that the number of carbon atoms is 1 to 12.

A $C_1$-$C_4$ alkyl group represents a linear or branched alkyl group having 1 to 4 carbon atoms. Examples of the $C_1$-$C_4$ alkyl group can include a methyl group, an ethyl group, a n-propyl group, an isopropyl group, a n-butyl group, a sec-butyl group, an isobutyl group, and a tert-butyl group.

Examples of preferred $C_1$-$C_4$ alkyl groups include a methyl group, an ethyl group, a n-propyl group, and an isopropyl group, and more preferably include a methyl group and an ethyl group.

A $C_1$-$C_6$ alkyl group represents a linear or branched alkyl group having 1 to 6 carbon atoms.
Examples of the $C_1$-$C_6$ alkyl group can include, but are not limited to, a methyl group, an ethyl group, a n-propyl group, an isopropyl group, a n-butyl group, a sec-butyl group, an isobutyl group, a tert-butyl group, a n-pentyl group, an isopentyl group, a neopentyl group, a n-hexyl group, and an isohexyl group.

Examples of preferred $C_1$-$C_6$ alkyl groups include a methyl group, an ethyl group, a n-propyl group, an isopropyl group, a n-butyl group, a sec-butyl group, an isobutyl group, a tert-butyl group, a n-pentyl group, and a n-hexyl group, and more preferably include a methyl group, an ethyl group, a n-propyl group, a n-butyl group, a n-pentyl group, and a n-hexyl group.

A $C_2$-$C_6$ alkenyl group represents a linear or branched alkenyl group having 2 to 6 carbon atoms. Examples of the $C_2$-$C_6$ alkenyl group can include, but are not limited to, a vinyl group, a 1-propenyl group, a 2-propenyl group, an isopropenyl group, a 1-butenyl group, a 2-butenyl group, a 3-butenyl group, a 1,3-butadienyl group, a 1-pentenyl group, a 2-pentenyl group, a 3-pentenyl group, a 4-pentenyl group, a 1,3-pentadienyl group, a 2,4-pentadienyl group, a 1-hexenyl group, a 2-hexenyl group, a 3-hexenyl group, a 4-hexenyl group, a 5-hexenyl group, a 1,3-hexadienyl group, a 1,4-hexadienyl group, a 1,5-hexadienyl group, a 2,4-hexadienyl group, a 2,5-hexadienyl group, a 3,5-hexadienyl group, and a 1,3,5-hexatrienyl group.

Examples of preferred $C_2$-$C_6$ alkenyl groups include a vinyl group, a 2-propenyl group, a 3-butenyl group, a 1,3-butadienyl group, a 4-pentenyl group, a 1,3-pentadienyl group, a 2,4-pentadienyl group, a 5-hexenyl group, a 1,3-hexadienyl group, a 2,4-hexadienyl group, a 3,5-hexadienyl group, and a 1,3,5-hexatrienyl group, and more preferably include a vinyl group, a 2-propenyl group, a 3-butenyl group, a 4-pentenyl group, and a 5-hexenyl group.

A $C_3$-$C_6$ cycloalkyl group represents a cyclic alkyl group having 3 to 6 carbon atoms. Examples of the $C_3$-$C_6$ cycloalkyl group can include a cyclopropyl group, a cyclobutyl group, a cyclopentyl group, and a cyclohexyl group.

Examples of preferred $C_3$-$C_6$ cycloalkyl groups include a cyclopropyl group, a cyclopentyl group, and a cyclohexyl group, and more preferably include a cyclopentyl group and a cyclohexyl group.

A $C_1$-$C_6$ alkoxy group represents a linear or branched alkoxy group having 1 to 6 carbon atoms. Examples of the $C_1$-$C_6$ alkoxy group can include, but are not limited to, a methoxy group, an ethoxy group, a n-propoxy group, an isopropoxy group, a n-butoxy group, a sec-butoxy group, an isobutoxy group, a t-butoxy group, a n-pentyloxy group, an isopentyloxy group, a neopentyloxy group, a n-hexyloxy group, and an isohexyloxy group.

Examples of preferred $C_1$-$C_6$ alkoxy groups include a methoxy group, an ethoxy group, a n-propoxy group, an isopropoxy group, a n-butoxy group, a sec-butoxy group, an isobutoxy group, a t-butoxy group, a n-pentyloxy group, and a n-hexyloxy group, more preferably include a methoxy group, an ethoxy group, a n-propoxy group, an isopropoxy group, a n-butoxy group, a n-pentyloxy group, and a n-hexyloxy group, and further preferably include a methoxy group, an ethoxy group, a n-propoxy group, and an isopropoxy group.

Examples of a $C_6$-$C_{10}$ aryl group can include, but are not limited to, phenyl and 1- or 2-naphthyl.

Examples of a $C_6$-$C_{10}$ aryl $C_1$-$C_4$ alkyl group can include, but are not limited to, a benzyl group.

"$R^3$ and $R^4$ may together form a ring" means that $R^3$ group and an $R^4$ group may together form a ring by forming a divalent group. Examples of the divalent group formed by the $R^3$ group and the $R^4$ group together can include, but are not limited to, $C_3$-$C_7$ alkylene groups (for example, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, and —CH$_2$CH$_2$CH$_2$CH$_2$CH$_2$CH$_2$CH$_2$—), —($C_1$-$C_3$ alkylene)-O—($C_1$-$C_3$ alkylene)- groups (for example, —CH$_2$CH$_2$—O—CH$_2$CH$_2$—), and —($C_1$-$C_3$ alkylene)-NH—($C_1$-$C_3$ alkylene)- groups (for example, —CH$_2$CH$_2$—NH—CH$_2$CH$_2$—). An alkylene group means a divalent group obtained by removing two hydrogens from a linear alkane. Examples of the alkylene group include a methylene group (—CH$_2$—), an ethylene group (—CH$_2$CH$_2$—), and a n-propylene group (—CH$_2$CH$_2$CH$_2$—). The alkylene group may be substituted with the substituent B as described above.

The substituent A herein represents a substituent selected from the group consisting of a $C_1$-$C_4$ alkyl group and a halogen atom.

The substituent B herein represents a substituent selected from the group consisting of a $C_1$-$C_4$ alkyl group, a halogen atom, and an oxo group.

2. A method for producing a mercaptophenol compound according to the present invention will be described.

(Step (i))

First, a step (i) will be described. The step (i) is the step of reacting a compound represented by formula (5):

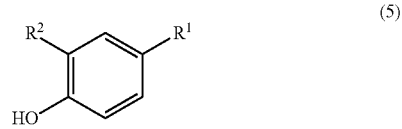

(5)

wherein $R^1$ and $R^2$ each independently represent a $C_1$-$C_4$ alkyl group or a halogen atom,
with a carbamoyl halide compound represented by formula (a):

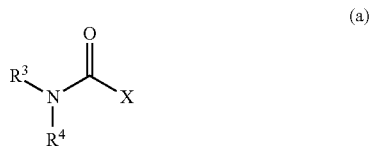

(a)

wherein $R^3$ and $R^4$ each independently represent a hydrogen atom, a $C_1$-$C_6$ alkyl group that may be substituted with one or two or more identical or different halogen atoms, a $C_2$-$C_6$ alkenyl group that may be substituted with one or two or more identical or different halogen atoms, a $C_3$-$C_6$ cycloalkyl group that may be substituted with one or two or more identical or different halogen atoms, a $C_1$-$C_6$ alkoxy group that may be substituted with one or two or more identical or different halogen atoms, a $C_6$-$C_{10}$ aryl group that may be substituted with one or two or more identical or different substituents A, or a $C_6$-$C_{10}$ aryl $C_1$-$C_4$ alkyl group that may be substituted with one or two or more identical or different substituents A,
or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B,
the substituent A represents a $C_1$-$C_4$ alkyl group or a halogen atom,
the substituent B represents a $C_1$-$C_4$ alkyl group, a halogen atom, or an oxo group, and
X represents a halogen atom,
in the presence of a base to produce a compound represented by formula (3):

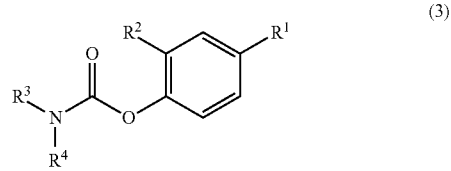

(3)

wherein $R^1$, $R^2$, $R^3$, and $R^4$ are as defined above.
The compounds, reaction conditions, and the like used in the step (i) will be described in detail below.

(Raw Material Compound)

The raw material used in the step (i) is a phenol compound represented by formula (5) and is a known compound or can be produced from a known compound by a known method. Examples of the compound of formula (5) include, but are not limited to, 2,4-dichlorophenol, 2,4-difluorophenol, 4-chloro-2-fluorophenol, 2-chloro-4-methylphenol, 2-fluoro-4-methylphenol, and 2,4-dimethylphenol.

(Carbamoyl Halide Compound)

The carbamoyl halide compound used in the step (i) is the compound represented by formula (a), and may be any carbamoyl halide compound as long as the reaction proceeds. Examples of the carbamoyl halide compound used in the step (i) include, but are not limited to, carbamoyl chloride, methylcarbamoyl chloride, dimethylcarbamoyl chloride, diethylcarbamoyl chloride, ethylmethylcarbamoyl chloride, dipropylcarbamoyl chloride, diisopropylcarbamoyl chloride, dibutylcarbamoyl chloride, diallylcarbamoyl chloride, bis(2-chloroethyl) carbamoyl chloride, N-methoxy-N-methylcarbamoyl chloride, diphenylcarbamoyl chloride, N-methyl-N-phenylcarbamoyl chloride, N-ethyl-N-phenylcarbamoyl chloride, N-benzyl-N-methylcarbamoyl chloride, pyrrolidine-1-carbonyl chloride, piperidine-1-carbonyl chloride, morpholine-4-carbonyl chloride, and 4-methylpiperazinecarbonyl chloride.

From the viewpoints of reactivity, yield, economic efficiency, and the like, examples of the carbamoyl halide compound in the step (i) preferably include dimethylcarbamoyl chloride, diethylcarbamoyl chloride, ethylmethylcarbamoyl chloride, dipropylcarbamoyl chloride, diisopropylcarbamoyl chloride, diphenylcarbamoyl chloride, N-methyl-N-phenylcarbamoyl chloride, pyrrolidine-1-carbonyl chloride, piperidine-1-carbonyl chloride, morpholine-4-carbonyl chloride, and 4-methylpiperazinecarbonyl chloride, more preferably include dimethylcarbamoyl chloride, diethylcarbamoyl chloride, diisopropylcarbamoyl chloride, and diphenylcarbamoyl chloride, and further preferably include dimethylcarbamoyl chloride and diethylcarbamoyl chloride.

(Amount of Carbamoyl Halide Compound Used)

The amount of the carbamoyl halide compound used in the step (i) may be any amount as long as the reaction proceeds. From the viewpoints of yield, by-product suppression, economic efficiency, and the like, the range of usually 0.01 to 10.0 mol, preferably 1.0 to 5.0 mol, more preferably 1.1 to 3.0 mol, and further preferably 1.2 to 2.0 mol relative to 1.0 mol of the compound of formula (5) can be illustrated.

(Base)

The base used in the step (i) may be any base as long as the reaction proceeds. Examples of the base used in the step (i) include, but are not limited to, metal alkoxides (for example, sodium methoxide, sodium ethoxide, and potassium tert-butoxide), alkali metal hydroxides (for example, lithium hydroxide, sodium hydroxide, and potassium hydroxide), alkaline earth metal hydroxides (for example, magnesium hydroxide, calcium hydroxide, and barium hydroxide), alkali metal carbonates (for example, lithium carbonate, sodium carbonate, and potassium carbonate), alkaline earth metal carbonates (for example, magnesium carbonate, calcium carbonate, and barium carbonate), alkali metal hydrogen carbonates (for example, lithium hydrogen carbonate, sodium hydrogen carbonate, and potassium hydrogen carbonate), alkaline earth metal hydrogen carbonates (for example, magnesium hydrogen carbonate and calcium hydrogen carbonate), phosphates (for example, sodium phosphate, potassium phosphate, and calcium phosphate), hydrogen phosphates (for example, sodium hydrogen phosphate, potassium hydrogen phosphate, and calcium hydrogen phosphate), and amines (for example, triethylamine, tributylamine, diisopropylethylamine, 1,8-diazabicyclo[5.4.0]-7-undec-7-ene (DBU), 1,4-diazabicyclo[2.2.2]octane (DABCO), N,N-dimethylaniline, N,N-diethylaniline, pyridine, 4-(dimethylamino)-pyridine, and 2,6-lutidine).

From the viewpoints of reactivity, yield, economic efficiency, and the like, examples of the base in the step (i) preferably include alkali metal carbonates, alkali metal hydrogen carbonates, and amines, and more preferably include amines.

Specific examples of the base in the step (i) preferably include sodium carbonate, potassium carbonate, sodium hydrogen carbonate, potassium hydrogen carbonate, triethylamine, tributylamine, diisopropylethylamine, 1,8-diazabicyclo[5.4.0]-7-undec-7-ene (DBU), 1,4-diazabicyclo[2.2.2]octane (DABCO), N,N-dimethylaniline, N,N-diethylaniline, pyridine, 4-(dimethylamino)-pyridine, and 2,6-lutidine, more preferably include triethylamine, diisopropylethylamine, 1,8-diazabicyclo[5.4.0]-7-undec-7-ene (DBU), 1,4-diazabicyclo[2.2.2]octane (DABCO), N,N-dimethylaniline, N,N-diethylaniline, pyridine, 4-(dimethylamino)-pyridine, and 2,6-lutidine, further preferably include triethylamine, diisopropylethylamine, N,N-dimethylaniline, N,N-diethylaniline, pyridine, 4-(dimethylamino)-pyridine, and 2,6-lutidine, and particularly preferably include triethylamine and 4-(dimethylamino)-pyridine.

The base in the step (i) may be used singly or in combination of two or more in any proportion. The form of the base in the step (i) may be any form as long as the reaction proceeds. Those skilled in the art can appropriately select the form of the base in the step (i).

(Amount of Base Used)

The amount of the base used in the step (i) may be any amount as long as the reaction proceeds. From the viewpoints of yield, by-product suppression, economic efficiency, and the like, for the amount of the base used in the step (i), the range of usually 0.01 to 10.0 equivalents, preferably 0.02 to 5.0 equivalents, more preferably 0.03 to 3.0 equivalents, and further preferably 0.05 to 2.0 equivalents relative to 1.0 mol of the compound of formula (5) can be illustrated.

(Solvent)

The step (i) is preferably performed using a solvent. The solvent used in the step (i) may be any solvent as long as the reaction proceeds. Examples of the solvent used in the step (i) include, but are not limited to, nitriles (for example, acetonitrile and propionitrile), ethers (for example, diethyl ether, diisopropyl ether, cyclopentyl methyl ether (CPME), tetrahydrofuran (THF), 1,4-dioxane, monoglyme, and diglyme), halogenated hydrocarbons (for example, dichloromethane, chloroform, carbon tetrachloride, dichloroethane, and tetrachloroethane), aromatic hydrocarbons (for example, benzene, chlorobenzene, dichlorobenzene, nitrobenzene, toluene, and xylene), amides (for example, N,N-dimethylformamide (DMF), N,N-dimethylacetamide (DMAC), and N-methylpyrrolidone (NMP)), imidazolinones (for example, 1,3-dimethyl-2-imidazolinone (DMI)), and sulfoxides (for example, dimethyl sulfoxide (DMSO)). These solvents can be used singly or as a mixed solvent in any mixing proportion.

From the viewpoints of reactivity, yield, economic efficiency, and the like, examples of the solvent in the step (i) preferably include nitriles, ethers, halogenated hydrocarbons, aromatic hydrocarbons, and amides, more preferably include nitriles, ethers, and halogenated hydrocarbons, and further preferably include halogenated hydrocarbons.

Specific examples of the solvent in the step (i) preferably include acetonitrile, propionitrile, diethyl ether, diisopropyl ether, cyclopentyl methyl ether (CPME), tetrahydrofuran (THF), 1,4-dioxane, monoglyme, diglyme, dichloromethane, chloroform, carbon tetrachloride, dichloroethane, tetrachloroethane, benzene, chlorobenzene, dichlorobenzene, nitrobenzene, toluene, xylene, N,N-dimethylformamide (DMF), N,N-dimethylacetamide (DMAC), and N-methylpyrrolidone (NMP), more preferably include acetonitrile, diethyl ether, diisopropyl ether, cyclopentyl methyl ether (CPME), tetrahydrofuran (THF), 1,4-dioxane, dichloromethane, chloroform, carbon tetrachloride, and dichloroethane, and further preferably include dichloromethane, chloroform, carbon tetrachloride, and dichloroethane.

(Amount of Solvent Used)

The amount of the solvent used in the step (i) may be any amount as long as the reaction proceeds. From the viewpoints of yield, by-product suppression, economic efficiency, and the like, the range of usually 0.01 to 50 L (liters), preferably 0.1 to 15 L, more preferably 0.1 to 10 L, and further preferably 0.1 to 5 L relative to 1.0 mol of the compound of formula (5) can be illustrated.

(Reaction Temperature)

The reaction temperature in the step (i) may be any temperature as long as the reaction proceeds. From the viewpoints of yield, by-product suppression, economic efficiency, and the like, as the reaction temperature, usually the range of $-20°$ C. (minus 20° C.) or higher and the boiling point of the solvent used or lower, preferably the range of $-20°$ C. or higher and 100° C. or lower, more preferably the range of $-10°$ C. or higher and 70° C. or lower, and further preferably the range of 0° C. or higher and 30° C. or lower can be illustrated.

(Reaction Time)

The reaction time in the step (i) is not particularly limited. Those skilled in the art can suitably adjust the reaction time in the step (i). From the viewpoints of yield, by-product suppression, economic efficiency, and the like, the range of usually 0.5 h to 48 h, preferably 0.5 h to 36 h, more preferably 1 h to 24 h, and further preferably 1 h to 12 h can be illustrated.

(Product)

The product produced in the step (i) is a phenyl carbamate compound represented by formula (3). Examples of the compound of formula (3) include, but are not limited to, 4-chloro-2-fluorophenyl dimethylcarbamate, 2,4-dimethylphenyl dimethylcarbamate, 2-chloro-4-methylphenyl dimethylcarbamate, 2-fluoro-4-methylphenyl dimethylcarbamate, 4-chloro-2-fluorophenyl diethylcarbamate, 2,4-dimethylphenyl diethylcarbamate, 2-chloro-4-methylphenyl diethylcarbamate, 2-fluoro-4-methylphenyl diethylcarbamate, 4-chloro-2-fluorophenyl diisopropylcarbamate, 2,4-dimethylphenyl diisopropylcarbamate, 2-chloro-4-methylphenyl diisopropylcarbamate, 2-fluoro-4-methylphenyl diisopropylcarbamate, 4-chloro-2-fluorophenyl diphenylcarbamate, 2,4-dimethylphenyl diphenylcarbamate, 2-chloro-4-methylphenyl diphenylcarbamate, 2-fluoro-4-methylphenyl diphenylcarbamate, 4-chloro-2-fluorophenyl N-methyl-N-phenylcarbamate, 4-chloro-2-fluorophenyl 1-pyrrolidinecarboxylate, 4-chloro-2-fluorophenyl 1-piperidinecarboxylate, 4-chloro-2-fluorophenyl 4-morpholinecarboxylate, and 4-chloro-2-fluorophenyl 4-methylpiperazinecarboxylate.

Examples of the product produced in the step (i) preferably include 4-chloro-2-fluorophenyl dimethylcarbamate, 2,4-dimethylphenyl dimethylcarbamate, 2-chloro-4-methylphenyl dimethylcarbamate, 2-fluoro-4-methylphenyl dimethylcarbamate, 4-chloro-2-fluorophenyl diethylcarbamate, 2,4-dimethylphenyl diethylcarbamate, 2-chloro-4-methylphenyl diethylcarbamate, 2-fluoro-4-methylphenyl diethylcarbamate, 4-chloro-2-fluorophenyl diisopropylcarbamate, 2,4-dimethylphenyl diisopropylcarbamate, 2-chloro-4-methylphenyl diisopropylcarbamate, 2-fluoro-4-methylphenyl diisopropylcarbamate, 4-chloro-2-fluorophenyl diphenylcarbamate, 2,4-dimethylphenyl diphenylcarbamate, 2-chloro-4-methylphenyl diphenylcarbamate, and 2-fluoro-4-methylphenyl diphenylcarbamate, more preferably include 4-chloro-2-fluorophenyl dimethylcarbamate, 2,4-dimethylphenyl dimethylcarbamate, 2-chloro-4-methylphenyl dimethylcarbamate, 2-fluoro-4-methylphenyl dimethylcarbamate, 4-chloro-2-fluorophenyl diethylcarbamate, 2,4-dimethylphenyl diethylcarbamate, 2-chloro-4-methylphenyl diethylcarbamate, and 2-fluoro-4-methylphenyl diethylcarbamate, and further preferably include 4-chloro-2-fluorophenyl dimethylcarbamate, 2,4-dimethylphenyl dimethylcarbamate, 4-chloro-2-fluorophenyl diethylcarbamate, and 2,4-dimethylphenyl diethylcarbamate.

(Step (ii))

Next, a step (ii) will be described. The step (ii) is the step of subjecting the compound represented by formula (3):

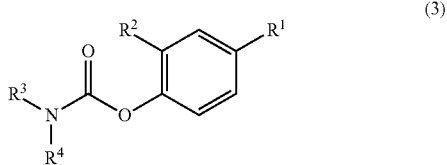

(3)

wherein $R^1$, $R^2$, $R^3$, and $R^4$ are as defined above, to a reaction with a sulfur compound in the presence of an acid to produce a compound represented by formula (2):

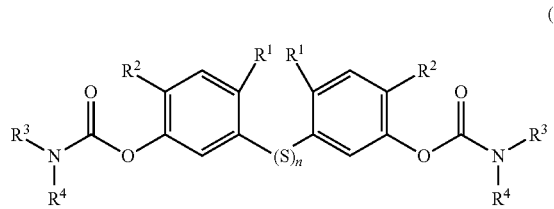

(2)

wherein $R^1$, $R^2$, $R^3$, and $R^4$ are as defined above, and n represents an integer of 2 or more. The compounds, reaction conditions, and the like used in the step (ii) will be described in detail below.

(Raw Material Compound)

The raw material used in the step (ii) is the phenyl carbamate compound represented by formula (3), and the product produced in the step (i) can be used.

(Sulfur Compound)

Examples of the sulfur compound used in the step (ii) include sulfur chloride compounds (for example, sulfur monochloride, sulfur dichloride, and trisulfur dichloride). When a sulfur chloride compound is used, a usually commercially available sulfur chloride compound may be used, or one produced by reacting sulfur with chlorine gas may be used.

As the sulfur compound used in the step (ii), sulfur monochloride is preferred. Sulfur monochloride is a compound represented by S—Cl or Cl—S—S—Cl and is also referred to as disulfur dichloride.

The form of the sulfur monochloride used in the present invention may be any form as long as the reaction proceeds. The form can be appropriately selected by those skilled in the art. For the sulfur monochloride, usually commercially available sulfur monochloride can be directly used, and the sulfur monochloride can also be used in a state of being dissolved in a solvent (Amount of Sulfur Monochloride Used)

Sulfur monochloride is considered herein as a compound represented by Cl—S—S—Cl, and the amount used is calculated assuming that 2 equivalents of sulfur atoms are generated from 1 mol of sulfur monochloride. The amount of sulfur monochloride used in the step (ii) may be any amount as long as the reaction proceeds. From the viewpoints of yield, by-product suppression, economic efficiency, and the like, the range of usually 0.01 to 10.0 equivalents, preferably 1.0 to 5.0 equivalents, more preferably 1.1 to 3.0 equivalents, and further preferably 1.2 to 2.0 equivalents relative to 1.0 mol of the compound of formula (3) can be illustrated.

(Acid)

Examples of the acid used in the step (ii) include Lewis acids generally known as catalysts for Friedel-Crafts reactions. Further, as long as the reaction proceeds, a hydrohalic acid (for example, hydrofluoric acid, hydrochloric acid, or hydrobromic acid), an inorganic acid (for example, sulfuric acid, nitric acid, phosphoric acid, or polyphosphoric acid), an organic acid (for example, formic acid, acetic acid, trifluoroacetic acid, methanesulfonic acid, or p-toluenesulfonic acid), a metal oxide (for example, alumina (aluminum (III) oxide)), an acidic ion exchange resin, acidic silica gel, or the like can also be used, but the acid used in the step (ii) is not limited to these.

Specific examples of the acid in the step (ii) preferably include aluminum chloride, aluminum bromide, aluminum iodide, iron(III) chloride, iron(III) bromide, cobalt(II) chloride, nickel(II) chloride, zinc(II) chloride, and boron trifluoride, more preferably include aluminum chloride, aluminum bromide, iron(III) chloride, zinc(II) chloride, and boron trifluoride, and further preferably include aluminum chloride.

The acid in the step (ii) may be used singly or in combination of two or more in any proportion. The form of the acid in the step (ii) may be any form as long as the reaction proceeds. Those skilled in the art can appropriately select the form of the acid in the step (ii). In addition, the Lewis acid may be an anhydride or a hydrate as long as the reaction proceeds sufficiently. An anhydride or a hydrate can be appropriately selected by those skilled in the art.

(Amount of Acid Used)

The amount of the acid used in the step (i) may be any amount as long as the reaction proceeds. From the viewpoints of yield, by-product suppression, economic efficiency, and the like, for the amount of the acid used in the step (i), the range of usually 0.01 to 10.0 equivalents, preferably 0.02 to 5.0 equivalents, more preferably 0.03 to 3.0 equivalents, and further preferably 0.05 to 2.0 equivalents relative to 1.0 mol of the compound of formula (3) can be illustrated.

(Solvent)

The step (ii) is preferably performed using a solvent. The solvent used in the step (ii) may be any solvent as long as the reaction proceeds. Examples of the solvent used in the step (ii) include, but are not limited to, nitriles (for example, acetonitrile and propionitrile), ethers (for example, diethyl ether, diisopropyl ether, cyclopentyl methyl ether (CPME), tetrahydrofuran (THF), 1,4-dioxane, monoglyme, and diglyme), halogenated hydrocarbons (for example, dichloromethane, chloroform, carbon tetrachloride, dichloroethane, and tetrachloroethane), aromatic hydrocarbons (for example, benzene, chlorobenzene, dichlorobenzene, nitrobenzene, toluene, and xylene), amides (for example, N,N-dimethylformamide (DMF), N,N-dimethylacetamide (DMAC), and N-methylpyrrolidone (NMP)), imidazolinones (for example, 1,3-dimethyl-2-imidazolinone (DMI)), and sulfoxides (for example, dimethyl sulfoxide (DMSO)). These solvents can be used singly or as a mixed solvent in any mixing proportion.

From the viewpoints of reactivity, yield, economic efficiency, and the like, examples of the solvent in the step (ii) preferably include nitriles, ethers, halogenated hydrocarbons, aromatic hydrocarbons, and amides, more preferably include nitriles, ethers, and halogenated hydrocarbons, and further preferably include halogenated hydrocarbons.

Specific examples of the solvent in the step (ii) preferably include acetonitrile, propionitrile, diethyl ether, diisopropyl ether, cyclopentyl methyl ether (CPME), tetrahydrofuran (THF), 1,4-dioxane, monoglyme, diglyme, dichloromethane, chloroform, carbon tetrachloride, dichloroethane, tetrachloroethane, benzene, chlorobenzene, dichlorobenzene, nitrobenzene, toluene, xylene, N,N-dimethylformamide (DMF), N,N-dimethylacetamide (DMAC), and N-methylpyrrolidone (NMP), more preferably include acetonitrile, diethyl ether, diisopropyl ether, cyclopentyl methyl ether (CPME), tetrahydrofuran (THF), 1,4-dioxane, dichloromethane, chloroform, carbon tetrachloride, and dichloroethane, and further preferably include dichloromethane, chloroform, carbon tetrachloride, and dichloroethane.

(Amount of Solvent Used)

The amount of the solvent used in the step (ii) may be any amount as long as the reaction proceeds. From the viewpoints of yield, by-product suppression, economic efficiency, and the like, the range of usually 0.01 to 50 L (liters), preferably 0.1 to 15 L, more preferably 0.1 to 10 L, and further preferably 0.1 to 5 L relative to 1.0 mol of the compound of formula (3) can be illustrated.

(Reaction Temperature)

The reaction temperature in the step (ii) may be any temperature as long as the reaction proceeds. From the viewpoints of yield, by-product suppression, economic efficiency, and the like, as the reaction temperature, usually the range of −20° C. (minus 20° C.) or higher and the boiling point of the solvent used or lower, preferably the range of −20° C. or higher and 100° C. or lower, more preferably the range of −10° C. or higher and 70° C. or lower, and further preferably the range of 0° C. or higher and 50° C. or lower can be illustrated.

(Reaction Time)

The reaction time in the step (ii) is not particularly limited. Those skilled in the art can suitably adjust the reaction time in the step (ii). From the viewpoints of yield, by-product suppression, economic efficiency, and the like, the range of usually 0.5 h to 48 h, preferably 0.5 h to 36 h, more preferably 1 h to 24 h, and further preferably 1 h to 12 h can be illustrated.

(Product)

The product produced in the step (ii) is a polysulfide compound represented by formula (2). The main component of the product produced in the step (ii) is a disulfide compound with n=2 in formula (2), but a polysulfide compound with n=3 or more is also confirmed as a product. In other words, the product produced in the step (ii) is obtained as a mixture of compounds with n=2 or more in formula (2).

The disulfide compound with n=2 and the polysulfide compound with n=3 or more provide a 5-mercaptophenyl carbamate compound represented by formula (1) that is the same product by a step (iii), the next step. Therefore, the disulfide compound with n=2 and the polysulfide compound with n=3 or more can be used as a raw material in the next step (iii) in a state of a mixture without each being isolated or purified. Examples of the disulfide compound of formula (2) include, but are not limited to, bis(5-dimethylcarbamoyloxy-2-chloro-4-fluorophenyl) disulfide, bis(5-dimethylcarbamoyloxy-2,4-dimethylphenyl) disulfide, bis(5-dimethylcarbamoyloxy-4-chloro-2-methylphenyl) disulfide, bis(5-dimethylcarbamoyloxy-4-fluoro-2-methylphenyl) disulfide, bis(5-diethylcarbamoyloxy-2-chloro-4-fluorophenyl) disulfide, bis(5-diethylcarbamoyloxy-2,4-dimethylphenyl) disulfide, bis(5-diethylcarbamoyloxy-4-chloro-2-methylphenyl) disulfide, bis(5-diethylcarbamoyloxy-4-fluoro-2-methylphenyl) disulfide, bis(5-isopropylcarbamoyloxy-2-chloro-4-fluorophenyl) disulfide, bis(5-isopropylcarbamoyloxy-2,4-dimethylphenyl) disulfide, bis(5-isopropylcarbamoyloxy-4-chloro-2-methylphenyl) disulfide, bis(5-isopropylcarbamoyloxy-4-fluoro-2-methylphenyl) disulfide, bis(5-diphenylcarbamoyloxy-2-chloro-4-fluorophenyl) disulfide, bis(5-diphenylcarbamoyloxy-2,4-dimethylphenyl) disulfide, bis(5-diphenylcarbamoyloxy-4-chloro-2-methylphenyl) disulfide, bis(5-diphenylcarbamoyloxy-4-fluoro-2-methylphenyl) disulfide, bis[5-(N-methyl-N-phenylcarbamoyloxy)-2-chloro-4-fluorophenyl] disulfide, bis[5-(1-pyrrolidinecarbonyloxy)-2-chloro-4-fluorophenyl] disulfide, bis[5-(1-piperidinecarbonyloxy)-2-chloro-4-fluorophenyl] disulfide, bis[5-(4-morpholinecarbonyloxy)-2-chloro-4-fluorophenyl] disulfide, and bis[5-(4-methylpiperazinecarbonyloxy)-2-chloro-4-fluorophenyl] disulfide.

Examples of the disulfide compound represented by formula (2) produced in the step (ii) preferably include bis(5-dimethylcarbamoyloxy-2-chloro-4-fluorophenyl) disulfide, bis(5-dimethylcarbamoyloxy-2,4-dimethylphenyl) disulfide, bis(5-dimethylcarbamoyloxy-4-chloro-2-methylphenyl) disulfide, bis(5-dimethylcarbamoyloxy-4-fluoro-2-methylphenyl) disulfide, bis(5-diethylcarbamoyloxy-2-chloro-4-fluorophenyl) disulfide, bis(5-diethylcarbamoyloxy-2,4-dimethylphenyl) disulfide, bis(5-diethylcarbamoyloxy-4-chloro-2-methylphenyl) disulfide, bis(5-diethylcarbamoyloxy-4-fluoro-2-methylphenyl) disulfide, bis(5-isopropylcarbamoyloxy-2-chloro-4-fluorophenyl) disulfide, bis(5-isopropylcarbamoyloxy-2,4-dimethylphenyl) disulfide, bis(5-isopropylcarbamoyloxy-4-chloro-2-methylphenyl) disulfide, bis(5-isopropylcarbamoyloxy-4-fluoro-2-methylphenyl) disulfide, bis(5-diphenylcarbamoyloxy-2-chloro-4-fluorophenyl) disulfide, bis(5-diphenylcarbamoyloxy-2,4-dimethylphenyl) disulfide, bis(5-diphenylcarbamoyloxy-4-chloro-2-methylphenyl) disulfide, and bis(5-diphenylcarbamoyloxy-4-fluoro-2-methylphenyl) disulfide, more preferably include bis(5-dimethylcarbamoyloxy-2-chloro-4-fluorophenyl) disulfide, bis(5-dimethylcarbamoyloxy-2,4-dimethylphenyl) disulfide, bis(5-dimethylcarbamoyloxy-4-chloro-2-methylphenyl) disulfide, bis(5-dimethylcarbamoyloxy-4-fluoro-2-methylphenyl) disulfide, bis(5-diethylcarbamoyloxy-2-chloro-4-fluorophenyl) disulfide, bis(5-diethylcarbamoyloxy-2,4-dimethylphenyl) disulfide, bis(5-diethylcarbamoyloxy-4-chloro-2-methylphenyl) disulfide, and bis(5-diethylcarbamoyloxy-4-fluoro-2-methylphenyl) disulfide, and further preferably include bis(5-dimethylcarbamoyloxy-2-chloro-4-fluorophenyl) disulfide, bis(5-dimethylcarbamoyloxy-2,4-dimethylphenyl) disulfide, bis(5-diethylcarbamoyloxy-2-chloro-4-fluorophenyl) disulfide, and bis(5-diethylcarbamoyloxy-2,4-dimethylphenyl) disulfide.

Examples of the polysulfide compound of formula (2) with n=3 or more produced in the step (ii) include, but are not limited to, bis(5-dimethylcarbamoyloxy-2-chloro-4-fluorophenyl) trisulfide, bis(5-dimethylcarbamoyloxy-2,4-dimethylphenyl) trisulfide, bis(5-dimethylcarbamoyloxy-4-chloro-2-methylphenyl) trisulfide, bis(5-dimethylcarbamoyloxy-4-fluoro-2-methylphenyl) trisulfide, bis(5-diethylcarbamoyloxy-2-chloro-4-fluorophenyl) trisulfide, bis(5-diethylcarbamoyloxy-2,4-dimethylphenyl) trisulfide, bis(5-diethylcarbamoyloxy-4-chloro-2-methylphenyl) trisulfide, bis(5-diethylcarbamoyloxy-4-fluoro-2-methylphenyl) trisulfide, bis(5-dimethylcarbamoyloxy-2-chloro-4-fluorophenyl) tetrasulfide, bis(5-dimethylcarbamoyloxy-2,4-dimethylphenyl) tetrasulfide, bis(5-dimethylcarbamoyloxy-4-chloro-2-methylphenyl) tetrasulfide, bis(5-dimethylcarbamoyloxy-4-fluoro-2-methylphenyl) tetrasulfide, bis(5-diethylcarbamoyloxy-2-chloro-4-fluorophenyl) tetrasulfide, bis(5-diethylcarbamoyloxy-2,4-dimethylphenyl) tetrasulfide, bis(5-diethylcarbamoyloxy-4-chloro-2-methylphenyl) tetrasulfide, bis(5-diethylcarbamoyloxy-4-fluoro-2-methylphenyl) tetrasulfide, bis(5-dimethylcarbamoyloxy-2-chloro-4-fluorophenyl) pentasulfide, bis(5-dimethylcarbamoyloxy-2,4-dimethylphenyl) pentasulfide, bis(5-dimethylcarbamoyloxy-4-chloro-2-methylphenyl) pentasulfide, bis(5-dimethylcarbamoyloxy-4-fluoro-2-methylphenyl) pentasulfide, bis(5-diethylcarbamoyloxy-2-chloro-4-fluorophenyl) pentasulfide, bis(5-diethylcarbamoyloxy-2,4-dimethylphenyl) pentasulfide, bis(5-diethylcarbamoyloxy-4-chloro-2-methylphenyl) pentasulfide, bis(5-diethylcarbamoyloxy-4-fluoro-2-methylphenyl) pentasulfide, bis(5-dimethylcarbamoyloxy-2-chloro-4-fluorophenyl) hexasulfide, bis(5-dimethylcarbamoyloxy-2,4-dimethylphenyl) hexasulfide, bis(5-dimethylcarbamoyloxy-4-chloro-2-methylphenyl) hexasulfide, bis(5-dimethylcarbamoyloxy-4-fluoro-2-methylphenyl) hexasulfide, bis(5-diethylcarbamoyloxy-2-chloro-4-fluorophenyl) hexasulfide, bis(5-diethylcarbamoyloxy-2,4-dimethylphenyl) hexasulfide, bis(5-diethylcarbamoyloxy-4-chloro-2-methylphenyl) hexasulfide, and bis(5-diethylcarbamoyloxy-4-fluoro-2-methylphenyl) hexasulfide.

(Step (iii))

Next, a step (iii) will be described. The step (iii) is the step of producing a compound represented by formula (1):

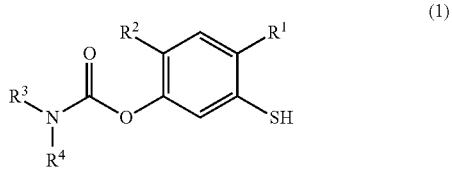

(1)

wherein $R^1$, $R^2$, $R^3$, and $R^4$ are as defined above, from the compound represented by formula (2):

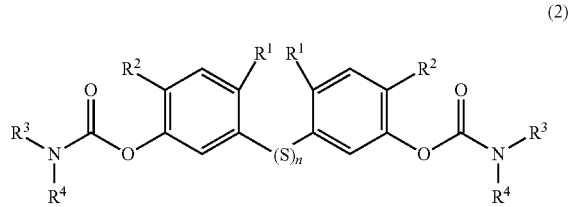

(2)

wherein $R^1$, $R^2$, $R^3$, $R^4$, and n are as defined above. The compounds, reaction conditions, and the like used in the step (iii) will be described in detail below.

(Raw Material Compound)

The raw material used in the step (iii) is the polysulfide compound represented by formula (2), and the product produced in the step (ii) can be used. The disulfide compound with n=2 and the polysulfide compound with n=3 or more provide a 5-mercaptophenyl carbamate compound represented by formula (1) that is the same product in the step (iii). Therefore, the disulfide compound with n=2 and the polysulfide compound with n=3 or more can be used as the raw material in the step (iii) in a state of a mixture without each being isolated or purified.

The step (iii) is preferably performed in the presence of a reducing agent and/or a base. Those skilled in the art can appropriately select whether the step (iii) is performed in the presence of a reducing agent, in the presence of a base, or in the presence of a reducing agent and a base.

(Reducing Agent)

The reducing agent used in the step (iii) may be any reducing agent as long as the reaction proceeds. Examples of the reducing agent used in the step (iii) include, but are not limited to, metals (for example, iron, zinc, and tin), aluminum hydride reagents (for example, lithium aluminum hydride and diisobutylaluminum hydride), borohydride reagents (for example, lithium borohydride, sodium borohydride, sodium cyanoborohydride, sodium triacetoxyborohydride, lithium tri(sec-butyl)borohydride, lithium triethylborohydride, potassium borohydride, and tetramethylammonium borohydride), borane complexes (for example, borane tetrahydrofuran complexes and borane triethylamine complexes), silane compounds (for example, trimethylsilane and triethylsilane), alkali metal sulfides (for example, sodium sulfide and potassium sulfide), alkali metal sulfites (for example, sodium sulfite and potassium sulfite), alkali metal hydrogen sulfites (for example, sodium hydrogen sulfite and potassium hydrogen sulfite), and alkali metal hydroxymethanesulfinates (for example, sodium hydroxymethanesulfinate).

From the viewpoints of reactivity, yield, economic efficiency, and the like, examples of the reducing agent in the step (iii) preferably include metals, borohydride reagents, alkali metal sulfides, alkali metal sulfites, alkali metal hydrogen sulfites, and alkali metal hydroxymethanesulfinates, more preferably include metals, borohydride reagents, alkali metal sulfides, and alkali metal hydroxymethanesulfinates, further preferably include alkali metal sulfides and alkali metal hydroxymethanesulfinates, and particularly preferably include alkali metal hydroxymethanesulfinates.

Specific examples of the reducing agent in the step (iii) preferably include iron, zinc, tin, lithium borohydride, sodium borohydride, sodium sulfide, potassium sulfide, sodium sulfite, potassium sulfite, sodium hydrogen sulfite, potassium hydrogen sulfite, and sodium hydroxymethanesulfinate, more preferably include iron, zinc, tin, lithium borohydride, sodium borohydride, sodium sulfide, potassium sulfide, and sodium hydroxymethanesulfinate, further preferably include sodium sulfide, potassium sulfide, and sodium hydroxymethanesulfinate, and particularly preferably include sodium hydroxymethanesulfinate.

Sodium hydroxymethanesulfinate is also referred to as sodium formaldehyde sulfoxylate. The sodium hydroxymethanesulfinate may be an anhydride or a hydrate as long as the reaction proceeds. From the viewpoints of reactivity, availability, ease of handling, and the like, sodium hydroxymethanesulfinate·dihydrate (trade name: Rongalite), a dihydrate, is preferred.

The reducing agent in the step (iii) may be used singly or in combination of two or more in any proportion. The form of the reducing agent in the step (iii) may be any form as long as the reaction proceeds. Those skilled in the art can appropriately select the form of the reducing agent. Examples of the form of the reducing agent include a liquid or a solid of only the reducing agent, or an aqueous solution or a solution of a solvent in the step (iii) described later, other than water.

(Amount of Reducing Agent Used)

The amount of the reducing agent used in the step (iii) may be any amount as long as the reaction proceeds. From the viewpoints of yield, by-product suppression, economic efficiency, and the like, the range of usually 0.1 to 10.0 equivalents, preferably 0.2 to 8.0 equivalents, more preferably 0.3 to 6.0 equivalents, and further preferably 0.5 to 4.0 equivalents relative to 1.0 mol of the compound of formula (2) can be illustrated.

(When Borohydride Reagent or the Like is Used as Reducing Agent)

When a borohydride reagent or the like is used as the reducing agent in the step (iii), it is preferably used in the presence of an alcohol. Examples of the alcohol include, but are not limited to, methanol, ethanol, and 2-propanol. The alcohol may be used singly or in combination of two or more in any proportion. The amount of the alcohol used may be any amount as long as the reaction proceeds. From the viewpoints of yield, by-product suppression, economic efficiency, and the like, the range of 1 to 10 mol relative to 1 mol of the compound of formula (2) can be illustrated, but those skilled in the art can suitably adjust the amount of the alcohol used. In addition, when the alcohol is also used as a solvent described later, a large excess amount of the alcohol may be used regardless of the range illustrated here.

(When Alkali Metal Hydroxymethanesulfinate is Used as Reducing Agent)

When an alkali metal hydroxymethanesulfinate is used as the reducing agent in the step (iii), it is preferably used in the presence of a base. The type, form, and amount of the base used can be appropriately selected by those skilled in the art with reference to the description of the base used in the step (iii) described later.

(Base)

The base used in the step (iii) may be any base as long as the reaction proceeds. Examples of the base used in the step (iii) include, but are not limited to, metal alkoxides (for example, sodium methoxide, sodium ethoxide, and potassium tert-butoxide), alkali metal hydroxides (for example, lithium hydroxide, sodium hydroxide, and potassium hydroxide), alkaline earth metal hydroxides (for example, magnesium hydroxide, calcium hydroxide, and barium hydroxide), alkali metal carbonates (for example, lithium carbonate, sodium carbonate, and potassium carbonate), alkaline earth metal carbonates (for example, magnesium carbonate, calcium carbonate, and barium carbonate), alkali metal hydrogen carbonates (for example, lithium hydrogen carbonate, sodium hydrogen carbonate, and potassium hydrogen carbonate), alkaline earth metal hydrogen carbonates (for example, magnesium hydrogen carbonate and calcium hydrogen carbonate), phosphates (for example, sodium phosphate, potassium phosphate, and calcium phosphate), hydrogen phosphates (for example, sodium hydrogen phosphate, potassium hydrogen phosphate, and calcium hydrogen phosphate), and amines (for example, triethylamine, tributylamine, diisopropylethylamine, 1,8-diazabicyclo[5.4.0]-7-undec-7-ene (DBU), 1,4-diazabicyclo[2.2.2]octane (DABCO), N,N-dimethylaniline, N,N-diethylaniline, pyridine, 4-(dimethylamino)-pyridine, and 2,6-lutidine).

From the viewpoints of reactivity, yield, economic efficiency, and the like, examples of the base in the step (iii) preferably include alkali metal hydroxides, alkali metal carbonates, and alkali metal hydrogen carbonates, more preferably include alkali metal carbonates and alkali metal hydrogen carbonates, and further preferably include alkali metal carbonates.

Specific examples of the base in the step (iii) preferably include lithium hydroxide, sodium hydroxide, potassium hydroxide, sodium carbonate, potassium carbonate, sodium hydrogen carbonate, and potassium hydrogen carbonate, more preferably include sodium carbonate, potassium carbonate, sodium hydrogen carbonate, and potassium hydrogen carbonate, and further preferably include sodium carbonate and potassium carbonate.

The base in the step (iii) may be used singly or in combination of two or more in any proportion, and those skilled in the art can appropriately select the combination of bases. The form of the base in the step (iii) may be any form as long as the reaction proceeds. Those skilled in the art can appropriately select the form of the base. Examples of the form of the base include a liquid or a solid of only the base, or an aqueous solution or a solution of a solvent in the step (iii) described later, other than water.

(Amount of Base Used)

The amount of the base used in the step (iii) may be any amount as long as the reaction proceeds. From the viewpoints of yield, by-product suppression, economic efficiency, and the like, for the amount of the base used, the range of usually 0.01 to 10.0 equivalents, preferably 0.02 to 5.0 equivalents, more preferably 0.03 to 4.0 equivalents, and further preferably 0.05 to 3.0 equivalents relative to 1.0 mol of the compound of formula (2) can be illustrated.

(Solvent)

The step (iii) is preferably performed using a solvent. The solvent used in the step (iii) may be any solvent as long as the reaction proceeds. Examples of the solvent used in the step (iii) include, but are not limited to, water, alcohols (for example, methanol, ethanol, 2-propanol, and butanol), nitriles (for example, acetonitrile and propionitrile), ethers (for example, diethyl ether, diisopropyl ether, cyclopentyl methyl ether (CPME), tetrahydrofuran (THF), 1,4-dioxane, monoglyme, and diglyme), ketones (for example, acetone, methyl ethyl ketone (MEK), methyl isopropyl ketone (MIPK), and methyl isobutyl ketone (MIBK)), carboxylates (for example, ethyl acetate and butyl acetate), halogenated hydrocarbons (for example, dichloromethane, chloroform, carbon tetrachloride, dichloroethane, and tetrachloroethane), aromatic hydrocarbons (for example, benzene, chlorobenzene, dichlorobenzene, nitrobenzene, toluene, and xylene), amides (for example, N,N-dimethylformamide (DMF), N,N-dimethylacetamide (DMAC), and N-methylpyrrolidone (NMP)), imidazolinones (for example, 1,3-dimethyl-2-imidazolinone (DMI)), and sulfoxides (for example, dimethyl sulfoxide (DMSO)). These solvents can be used singly or as a mixed solvent in any mixing proportion.

From the viewpoints of reactivity, yield, economic efficiency, and the like, examples of the solvent in the step (iii) preferably include water, alcohols, nitriles, ethers, ketones, carboxylates, halogenated hydrocarbons, aromatic hydrocarbons, and amides, more preferably include water, nitriles, ethers, ketones, halogenated hydrocarbons, and aromatic hydrocarbons, and further preferably include water and aromatic hydrocarbons.

Specific examples of the solvent in the step (iii) preferably include water, methanol, ethanol, 2-propanol, butanol, acetonitrile, propionitrile, diethyl ether, diisopropyl ether, cyclopentyl methyl ether (CPME), tetrahydrofuran (THF), 1,4-dioxane, monoglyme, diglyme, acetone, methyl ethyl ketone (MEK), methyl isopropyl ketone (MIPK), methyl isobutyl ketone (MIBK), ethyl acetate, butyl acetate, dichloromethane, chloroform, carbon tetrachloride, dichloroethane, tetrachloroethane, benzene, chlorobenzene, dichlorobenzene, nitrobenzene, toluene, xylene, N,N-dimethylformamide (DMF), N,N-dimethylacetamide (DMAC), and N-methylpyrrolidone (NMP), more preferably include water, acetonitrile, diethyl ether, diisopropyl ether, cyclopentyl methyl ether (CPME), tetrahydrofuran (THF), 1,4-dioxane, methyl isobutyl ketone (MIBK), dichloromethane, chloroform, carbon tetrachloride, dichloroethane, chlorobenzene, dichlorobenzene, toluene, and xylene, and further preferably include water, chlorobenzene, dichlorobenzene, toluene, and xylene.

(Amount of Solvent Used)

The amount of the solvent used in the step (iii) may be any amount as long as the reaction proceeds. From the viewpoints of yield, by-product suppression, economic efficiency, and the like, the range of usually 0.01 to 50 L (liters), preferably 0.1 to 15 L, more preferably 0.1 to 10 L, and further preferably 0.1 to 5 L relative to 1.0 mol of the compound of formula (2) can be illustrated.

(Phase Transfer Catalyst)

When the reaction in the step (iii) is performed in a mixed solvent of water and another organic solvent, it may be performed in the presence or absence of a phase transfer catalyst. Whether a phase transfer catalyst is used or not can be appropriately determined by those skilled in the art. Examples of the phase transfer catalyst include, but are not limited to, quaternary ammonium salts (for example, tetrabutylammonium bromide, tetrabutylammonium hydrogen sulfate, and trimethylbenzylammonium chloride), quaternary phosphonium salts (for example, tetrabutylphosphonium bromide, tetraoctylphosphonium bromide, and tetraphenylphosphonium bromide), and crown ethers (for example, 12-crown-4, 15-crown-5, and 18-crown-6).

From the viewpoints of reactivity, yield, economic efficiency, and the like, examples of the phase transfer catalyst preferably include quaternary ammonium salts and quaternary phosphonium salts, and more preferably include quaternary ammonium salts.

Specific examples of the phase transfer catalyst in the step (iii) preferably include tetramethylammonium chloride, tetramethylammonium bromide, tetrabutylammonium chloride, tetrabutylammonium bromide, tetrabutylammonium iodide, tetrabutylammonium hydroxide, tetrabutylammonium hydrogen sulfate, tributylmethylammonium chloride, tributylmethylammonium bromide, trimethylbenzylammonium chloride, trimethylbenzylammonium bromide, trimethylbenzylammonium hydroxide, triethylbenzylammonium chloride, triethylbenzylammonium bromide, lauryltrimethylammonium chloride, lauryltrimethylammonium bromide, benzyllauryldimethylammonium chloride, benzyllauryldimethylammonium bromide, trioctylmethylammonium chloride, trioctylmethylammonium bromide, trioctylethylammonium chloride, trioctylethylammonium bromide, benzyldimethyloctadecylammonium chloride, benzyldimethyloctadecylammonium bromide, myristyltrimethylammonium bromide, N,N-dimethylpyrrolidinium chloride, N,N-dimethylpiperidinium iodide, N-ethyl-N-methylpyrrolidinium bromide, N-ethyl-N-methylpyrrolidinium iodide, N-butyl-N-methylpyrrolidinium bromide, N-benzyl-N-methylpyrrolidinium chloride, N-butyl-N-methylmorpholinium bromide, N-butyl-N-methylmorpholinium iodide, N-allyl-N-methylmorpholinium bromide, N-methyl-N-ethylpiperidinium acetate, N-methyl-N-ethylpiperidinium iodide, N-methyl-N-benzylpiperidinium chloride, N-methyl-N-benzylpiperidinium bromide, tetrabutylphosphonium bromide, tetraoctylphosphonium bromide, and tetraphenylphosphonium bromide, and more preferably include tetrabutylammonium bromide, tetrabutylammonium hydrogen sulfate, trimethylbenzylammonium chloride, trimethylbenzylammonium bromide, trioctylmethylammonium chloride, trioctylmethylammonium bromide, benzyllauryldimethylammonium chloride, benzyldimethyloctadecylammonium chloride, benzyldimethyloctadecylammonium bromide, and myristyltrimethylammonium bromide.

(Amount of Phase Transfer Catalyst Used)

The amount of the phase transfer catalyst used in the step (iii) may be any amount as long as the reaction proceeds. The amount of the phase transfer catalyst used in the step (iii) can be appropriately adjusted by those skilled in the art. From the viewpoints of yield, by-product suppression, economic efficiency, and the like, the range of usually 0.01 equivalents to 1.0 equivalent, preferably 0.03 equivalents to 0.8 equivalents, and more preferably 0.05 equivalents to 0.5 equivalents relative to 1.0 mol of the compound of formula (2) can be illustrated.

The phase transfer catalyst may be used singly or in combination of two or more in any proportion. The form of the phase transfer catalyst may be any form as long as the reaction proceeds. Those skilled in the art can appropriately select the form of the phase transfer catalyst.

(Reaction Temperature)

The reaction temperature in the step (iii) may be any temperature as long as the reaction proceeds. From the viewpoints of yield, by-product suppression, economic efficiency, and the like, as the reaction temperature, usually the range of −20° C. (minus 20° C.) or higher and the boiling point of the solvent used or lower, preferably the range of −20° C. or higher and 100° C. or lower, more preferably the range of −10° C. or higher and 70° C. or lower, and further preferably the range of 0° C. or higher and 50° C. or lower can be illustrated.

(Reaction Time)

The reaction time in the step (iii) is not particularly limited. Those skilled in the art can suitably adjust the reaction time in the step (iii). From the viewpoints of yield, by-product suppression, economic efficiency, and the like, the range of usually 0.5 h to 48 h, preferably 0.5 h to 36 h, more preferably 1 h to 24 h, and further preferably 1 h to 12 h can be illustrated.

(Product)

The product produced in the step (iii) is a 5-mercaptophenyl carbamate compound represented by formula (1). Examples of the 5-mercaptophenyl carbamate compound of formula (1) include, but are not limited to, 4-chloro-2-fluoro-5-mercaptophenyl dimethylcarbamate, 5-mercapto-2,4-dimethylphenyl dimethylcarbamate, 2-chloro-5-mercapto-4-methylphenyl dimethylcarbamate, 2-fluoro-5-mercapto-4-methylphenyl dimethylcarbamate, 4-chloro-2-fluoro-5-mercaptophenyl diethylcarbamate, 5-mercapto-2,4-dimethylphenyl diethylcarbamate, 2-chloro-5-mercapto-4-methylphenyl diethylcarbamate, 2-fluoro-5-mercapto-4-methylphenyl diethylcarbamate, 4-chloro-2-fluoro-5-mercaptophenyl diisopropylcarbamate, 5-mercapto-2,4-dimethylphenyl diisopropylcarbamate, 2-chloro-5-mercapto-4-methylphenyl diisopropylcarbamate, 2-fluoro-5-mercapto-4-methylphenyl diisopropylcarbamate, 4-chloro-2-fluoro-5-mercaptophenyl diphenylcarbamate, 5-mercapto-2,4-dimethylphenyl diphenylcarbamate, 2-chloro-5-mercapto-4-methylphenyl diphenylcarbamate, 2-fluoro-5-mercapto-4-methylphenyl diphenylcarbamate, 4-chloro-2-fluoro-5-mercaptophenyl N-methyl-N-phenylcarbamate, 4-chloro-2-fluoro-5-mercaptophenyl 1-pyrrolidinecarboxylate, 4-chloro-2-fluoro-5-mercaptophenyl 1-piperidinecarboxylate, 4-chloro-2-fluoro-5-mercaptophenyl 4-morpholinecarboxylate, and 4-chloro-2-fluoro-5-mercaptophenyl 4-methylpiperazinecarboxylate.

Examples of the product produced in the step (iii) preferably include 4-chloro-2-fluoro-5-mercaptophenyl dimethylcarbamate, 5-mercapto-2,4-dimethylphenyl dimethylcarbamate, 2-chloro-5-mercapto-4-methylphenyl dimethylcarbamate, 2-fluoro-5-mercapto-4-methylphenyl dimethylcarbamate, 4-chloro-2-fluoro-5-mercaptophenyl diethylcarbamate, 5-mercapto-2,4-dimethylphenyl diethylcarbamate, 2-chloro-5-mercapto-4-methylphenyl diethylcarbamate, 2-fluoro-5-mercapto-4-methylphenyl diethylcarbamate, 4-chloro-2-fluoro-5-mercaptophenyl diisopropylcarbamate, 5-mercapto-2,4-dimethylphenyl diisopropylcarbamate, 2-chloro-5-mercapto-4-methylphenyl diisopropylcarbamate, 2-fluoro-5-mercapto-4-methylphenyl diisopropylcarbamate, 4-chloro-2-fluoro-5-mercaptophenyl diphenylcarbamate, 5-mercapto-2,4-dimethylphenyl diphenylcarbamate, 2-chloro-5-mercapto-4-methylphenyl diphenylcarbamate, and 2-fluoro-5-mercapto-4-methylphenyl diphenylcarbamate, more preferably include 4-chloro-2-fluoro-5-mercaptophenyl dimethylcarbamate, 5-mercapto-2,4-dimethylphenyl dimethylcarbamate, 2-chloro-5-mercapto-4-methylphenyl dimethylcarbamate, 2-fluoro-5-mercapto-4-methylphenyl dimethylcarbamate, 4-chloro-2-fluoro-5-mercaptophenyl diethylcarbamate, 5-mercapto-2,4-dimethylphenyl diethylcarbamate, 2-chloro-5-mercapto-4-methylphenyl diethylcarbamate, and 2-fluoro-5-mercapto-4-methylphenyl diethylcarbamate, and further preferably include 4-chloro-2-fluoro-5-mercaptophenyl dimethylcarbamate, 5-mercapto-2,4-dimethylphenyl dimethylcarbamate, 4-chloro-2-fluoro-5-mercaptophenyl diethylcarbamate, and 5-mercapto-2,4-dimethylphenyl diethylcarbamate.

(Step (iv))

Next, a step (iv) will be described. The step (iv) is the step of producing a compound represented by formula (4):

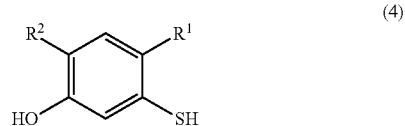

(4)

wherein $R^1$ and $R^2$ are as defined above,
from the compound represented by formula (1):

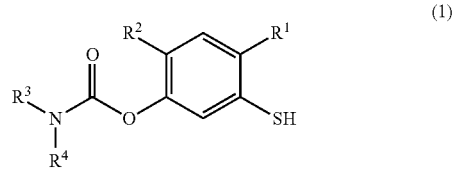

(1)

wherein $R^1$, $R^2$, $R^3$, and $R^4$ are as defined above. The compounds, reaction conditions, and the like used in the step (iv) will be described in detail below.

(Raw Material Compound)

The raw material used in the step (iv) is the 5-mercaptophenyl carbamate compound represented by formula (1), and the product produced in the step (iii) can be used. For the raw material used in the step (iv), the compound of formula (1) may be used as it is, and a salt of the compound of formula (1) can also be previously prepared and then used in the step (iv). When a salt of the compound of formula (1) is prepared and then used in the step (iv), the salt of the compound of formula (1) may be isolated and then used in the step (iv), or may be used in the step (iv) as an aqueous solution or a solution of a solvent described later, without isolation. The salt of the compound of formula (1) can be prepared, for example, by reacting the compound of formula (1) with an appropriate base.

(Base)

In the reaction in the step (iv), as long as its object is achieved, a base may be used. Whether a base is used can be appropriately selected by those skilled in the art. The base used in the step (iv) may be any base as long as the reaction proceeds. Examples of the base used in the step (iv) include, but are not limited to, metal alkoxides (for example, sodium methoxide, sodium ethoxide, and potassium tert-butoxide), alkali metal hydroxides (for example, lithium hydroxide, sodium hydroxide, and potassium hydroxide), alkaline earth metal hydroxides (for example, magnesium hydroxide, calcium hydroxide, and barium hydroxide), alkali metal carbonates (for example, lithium carbonate, sodium carbonate, and potassium carbonate), alkaline earth metal carbonates (for example, magnesium carbonate, calcium carbonate, and barium carbonate), alkali metal hydrogen carbonates (for example, lithium hydrogen carbonate, sodium hydrogen carbonate, and potassium hydrogen carbonate), alkaline earth metal hydrogen carbonates (for example, magnesium hydrogen carbonate and calcium hydrogen carbonate), phosphates (for example, sodium phosphate, potassium phosphate, and calcium phosphate), hydrogen phosphates (for example, sodium hydrogen phosphate, potassium hydrogen phosphate, and calcium hydrogen phosphate), and amines (for example, triethylamine, tributylamine, diisopropylethylamine, 1,8-diazabicyclo[5.4.0]-7-undec-7-ene (DBU), 1,4-diazabicyclo[2.2.2]octane (DABCO), N,N-dimethylaniline, N,N-diethylaniline, pyridine, 4-(dimethylamino)-pyridine, and 2,6-lutidine).

From the viewpoints of reactivity, yield, economic efficiency, and the like, examples of the base in the step (iv) preferably include metal alkoxides, alkali metal hydroxides, alkaline earth metal hydroxides, alkali metal carbonates, and alkali metal hydrogen carbonates, more preferably include metal alkoxides, alkali metal hydroxides, alkali metal carbonates, and alkali metal hydrogen carbonates, and further preferably include alkali metal hydroxides and alkali metal carbonates.

Specific examples of the base in the step (iv) preferably include sodium methoxide, sodium ethoxide, potassium tert-butoxide, lithium hydroxide, sodium hydroxide, potassium hydroxide, magnesium hydroxide, calcium hydroxide, sodium carbonate, potassium carbonate, sodium hydrogen carbonate, and potassium hydrogen carbonate, more preferably include potassium tert-butoxide, lithium hydroxide, sodium hydroxide, potassium hydroxide, sodium carbonate, potassium carbonate, sodium hydrogen carbonate, and potassium hydrogen carbonate, and further preferably include lithium hydroxide, sodium hydroxide, potassium hydroxide, sodium carbonate, and potassium carbonate.

The base in the step (iv) may be used singly or in combination of two or more in any proportion. The form of the base in the step (iv) may be any form as long as the reaction proceeds. Those skilled in the art can appropriately select the form of the base in the step (iv).

(Amount of Base Used)

The amount of the base used in the step (iv) may be any amount as long as the reaction proceeds. From the viewpoints of yield, by-product suppression, economic efficiency, and the like, for the amount of the base used in the step (iv), the range of usually 0.01 to 20.0 equivalents, preferably 0.1 to 15.0 equivalents, more preferably 0.5 to 10.0 equivalents, and further preferably 1.0 to 5.0 equivalents relative to 1.0 mol of the compound of formula (1) can be illustrated. In addition, when the salt of the compound of formula (1) is prepared and then used in the step (iv), it may be used with the amount of the base for preparing the salt of the compound of formula (1) added to the above amount of the base used.

(Solvent)

The step (iv) is preferably performed using a solvent. The solvent used in the step (iv) may be any solvent as long as the reaction proceeds. Examples of the solvent used in the step (iv) include, but are not limited to, water, alcohols (for example, methanol, ethanol, 2-propanol, and butanol), nitriles (for example, acetonitrile and propionitrile), ethers (for example, diethyl ether, diisopropyl ether, cyclopentyl methyl ether (CPME), tetrahydrofuran (THF), 1,4-dioxane, monoglyme, and diglyme), ketones (for example, acetone, methyl ethyl ketone (MEK), methyl isopropyl ketone (MIPK), and methyl isobutyl ketone (MIBK)), halogenated hydrocarbons (for example, dichloromethane, chloroform, carbon tetrachloride, dichloroethane, and tetrachloroethane), aromatic hydrocarbons (for example, benzene, chlorobenzene, dichlorobenzene, nitrobenzene, toluene, and xylene), amides (for example, N,N-dimethylformamide (DMF), N,N-dimethylacetamide (DMAC), and N-methylpyrrolidone (NMP)), imidazolinones (for example, 1,3-dimethyl-2-imidazolinone (DMI)), and sulfoxides (for example, dimethyl sulfoxide (DMSO)). These solvents can be used singly or as a mixed solvent in any mixing proportion.

From the viewpoints of reactivity, yield, economic efficiency, and the like, examples of the solvent in the step (iv) preferably include water, alcohols, nitriles, ethers, ketones, halogenated hydrocarbons, aromatic hydrocarbons, and amides, more preferably include water, ethers, ketones, halogenated hydrocarbons, and aromatic hydrocarbons, and further preferably include water and aromatic hydrocarbons.

Specific examples of the solvent in the step (iv) preferably include water, methanol, ethanol, 2-propanol, butanol, acetonitrile, propionitrile, diethyl ether, diisopropyl ether, cyclopentyl methyl ether (CPME), tetrahydrofuran (THF), 1,4-dioxane, monoglyme, diglyme, acetone, methyl ethyl ketone (MEK), methyl isopropyl ketone (MIPK), methyl isobutyl ketone (MIBK), dichloromethane, chloroform, carbon tetrachloride, dichloroethane, tetrachloroethane, benzene, chlorobenzene, dichlorobenzene, nitrobenzene, toluene, xylene, N,N-dimethylformamide (DMF), N,N-dimethylacetamide (DMAC), and N-methylpyrrolidone (NMP), more preferably include water, diethyl ether, diisopropyl ether, cyclopentyl methyl ether (CPME), tetrahydrofuran (THF), 1,4-dioxane, methyl isobutyl ketone (MIBK), dichloromethane, chloroform, carbon tetrachloride, dichloroethane, chlorobenzene, dichlorobenzene, toluene, and xylene, and further preferably include water, chlorobenzene, dichlorobenzene, toluene, and xylene.

(Amount of Solvent Used)

The amount of the solvent used in the step (iv) may be any amount as long as the reaction proceeds. From the viewpoints of yield, by-product suppression, economic efficiency, and the like, the range of usually 0.01 to 50 L (liters), preferably 0.1 to 15 L, more preferably 0.1 to 10 L, and further preferably 0.1 to 5 L relative to 1.0 mol of the compound of formula (1) can be illustrated.

(Reaction Temperature)

The reaction temperature in the step (iv) may be any temperature as long as the reaction proceeds. From the viewpoints of yield, by-product suppression, economic efficiency, and the like, as the reaction temperature, usually the range of −20° C. (minus 20° C.) or higher and the boiling point of the solvent used or lower, preferably the range of −20° C. or higher and 100° C. or lower, can be illustrated.

(Reaction Time)

The reaction time in the step (iv) is not particularly limited. Those skilled in the art can suitably adjust the reaction time in the step (iv). From the viewpoints of yield, by-product suppression, economic efficiency, and the like, the range of usually 0.1 h to 48 h, preferably 0.1 h to 36 h, more preferably 0.1 h to 24 h, and further preferably 0.1 h to 12 h can be illustrated.

(Product)

The product produced in the step (iv) is a mercaptophenol compound represented by formula (4). In the step (iv), the mercaptophenol compound represented by formula (4) can be produced by treating, with an appropriate acid, a salt of the mercaptophenol compound represented by formula (4) obtained by the reaction of the compound of formula (1) or the salt of the compound of formula (1) with the base. Examples of the compound of formula (4) include, but are not limited to, 4-chloro-2-fluoro-5-mercaptophenol, 5-mercapto-2,4-dimethylphenol, 2-chloro-5-mercapto-4-methylphenol, and 2-fluoro-5-mercapto-4-methylphenol.

EXAMPLES

Next, the production method of the present invention will be specifically described by giving Examples, but the present invention is not limited by these Examples in any way.

In the following Examples, room temperature is usually in the range of 10° C. to 35° C.

For the measurement of physical properties in the Examples and Reference Examples herein, the following equipment was used.

($^1$H Nuclear Magnetic Resonance Spectrum ($^1$H-NMR)) Varian Mercury-300, internal standard substance: tetramethylsilane (TMS)

(HPLC: High Performance Liquid Chromatography) pump: LC-2010A (manufactured by SHIMADZU CORPORATION), column: CERI L-column ODS (4.6×250 mm), L-C18, 5 μm, 12 nm Regarding the HPLC analysis method, the following literatures can be referred to as needed.

(a): The Chemical Society of Japan ed., "Shin Jikkenkagaku Koza (New Experimental Chemistry Course) 9 Bunsekikagaku (Analytical Chemistry) II", pp. 86-112 (1977), published by Shingo Iizumi, Maruzen Co., Ltd. (For example, regarding combinations of packing materials and mobile phases that can be used in the column, pp. 93-96 can be referred to.)

(b): The Chemical Society of Japan ed., "Jikkenkagaku Koza (Experimental Chemistry Course) 20-1 Bunsekikagaku (Analytical Chemistry)", 5th ed., pp. 130-151 (2007), published by Seishiro Murata, Maruzen Co., Ltd. (For example, regarding a specific usage and specific conditions of reversed phase chromatography analysis, pp. 135-137 can be referred to.)

(LC/MS: Liquid Chromatography Mass Spectrometry) pump: Waters Acquity H Class, detector: Waters Q-Tof Premier, column: CERI L-column ODS (4.6×250 mm), L-C18, 5 μm, 12 nm (Method for Measuring pH)

The pH was measured by a glass electrode type hydrogen ion concentration indicator. As the glass electrode type hydrogen ion concentration indicator, for example, type: HM-20P manufactured by DKK-TOA CORPORATION can be used.

(Method for Measuring Melting Point)

The melting point was measured by a DSC differential scanning calorimeter. The differential scanning calorimetry analysis was performed in the temperature range of 10 to 400° C. at a heating rate of 10° C./min using model: DSC-60 (manufactured by SHIMADZU CORPORATION). Regarding the differential scanning calorimetry method, the following literatures can be referred to as needed.

(a): The Chemical Society of Japan ed., "Daiyonhan (4th ed.) Jikkenkagaku Koza (Experimental Chemistry Course) 4 Netsu, Atsuryoku (Heat and Pressure)", pp. 57-93 (1992), published by Kumao Ebihara, Maruzen Co., Ltd.

(b): The Chemical Society of Japan ed., "Daigohan (5th ed.) Jikkenkagaku Koza (Experimental Chemistry Course) 6 Ondo•Netsu, Atsuryoku (Temperature and Heat and Pressure)", pp. 203-205 (2005), published by Seishiro Murata, Maruzen Co., Ltd.

Example 1

Production of 4-Chloro-2-fluorophenyl N,N-Dimethylcarbamate

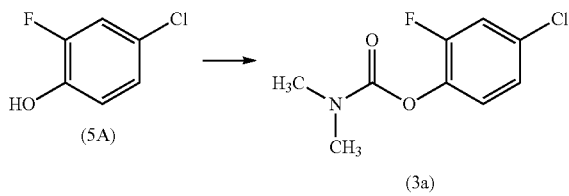

293 g (2.00 mol) of 4-chloro-2-fluorophenol, 12.2 g (0.100 mol) of 4-dimethylaminopyridine, 258 g (2.40 mol) of dimethylcarbamoyl chloride, and 1.43 L of dichloromethane were added to a 3 L four-necked flask equipped with a stirrer, a reflux condenser, a thermometer, and a dropping funnel, and stirred. After the mixture was dissolved, 263 g (2.60 mol) of triethylamine was dropped at room temperature over 1 h, and further the mixture was stirred at room temperature for 5 h. The end of the reaction was confirmed. 400 mL of water and 62.5 g of 35% hydrochloric acid were added to the reaction mixture, and the mixture was stirred at room temperature for 30 min. Then, the mixture was separated into an organic layer and an aqueous layer, and 450 mL of water and 381 g of a 5% sodium hydrogen carbonate aqueous solution were added to the obtained organic layer. The mixture was stirred at room temperature for 30 min to wash the organic layer. Then, the mixture was separated into an organic layer and an aqueous layer, and for the obtained organic layer, the dichloromethane was distilled off under reduced pressure at 60° C. 400 mL of isopropyl alcohol was added to the obtained residue to precipitate crystals of the target compound, and then further 640 mL of water was dropped over 4 h. The suspension of the crystals was stirred at 10° C. for 1 h, and then the crystals were filtered off and dried to obtain 404 g (yield 93%) of 4-chloro-2-fluorophenyl N,N-dimethylcarbamate as white crystals.

$^1$H-NMR (300 MHz, CDCl3) δ (ppm): 7.19-7.08 (m, 3H), 3.11 (s, 3H), 3.02 (s, 3H)

Melting point: 47.6° C.

Among many similar compounds, particularly a phenyl carbamate compound such as the compound (3a) obtained in Example 1 had high crystallinity.

Example 2

Production of Bis(5-dimethylcarbamoyloxy-2-chloro-4-fluorophenyl) Disulfide

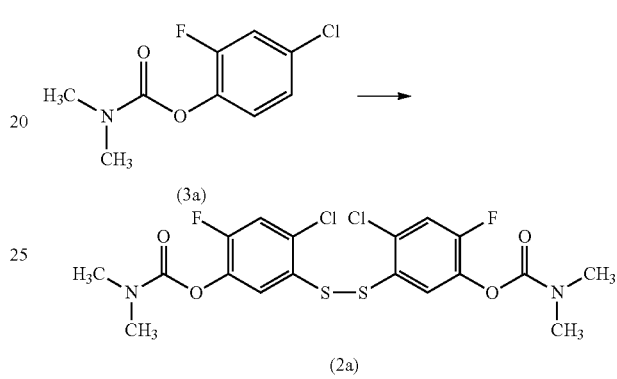

90 mL of dichloromethane and 60.0 g (0.45 mol) of aluminum chloride were added to a 300 mL four-necked flask equipped with a stirrer, a reflux condenser, a thermometer, and a dropping funnel. Next, while the mixture was stirred at room temperature, a solution of 65.3 g (0.30 mol) of 4-chloro-2-fluorophenyl N,N-dimethylcarbamate in 60 mL of dichloromethane was dropped. Then, 30.4 g (0.225 mol) of sulfur monochloride was dropped into the mixture at 40° C. over 3 h, and further the mixture was stirred for 1 h.

279 mL of water and 121 mL of dichloromethane were added to a 1 L four-necked flask equipped with a stirrer, a reflux condenser, a thermometer, and a dropping funnel, and the reaction mixture obtained above was dropped thereinto at room temperature. The mixture was stirred at room temperature for 30 min. Then, the mixture was separated into an organic layer and an aqueous layer, and for the obtained organic layer, the dichloromethane was distilled off under reduced pressure at 60° C. 300 mL of toluene was added to the obtained residue, and then 124 mL of water and 156 g of 35% hydrochloric acid were added at 60° C., and the mixture was stirred for 30 min to wash the organic layer. The same washing operation was performed using each of 286 g of a 5% sodium hydrogen carbonate aqueous solution and 279 g of 15% brine, to obtain the target compound as a toluene solution. When the components of the obtained toluene solution were analyzed using LC-MS, the presence of a trisulfide compound, a tetrasulfide compound, and a pentasulfide compound was also confirmed in addition to a disulfide compound.

($^1$H-NMR Shift of Disulfide Compound)

$^1$H-NMR (300 MHz, CDCl3) δ (ppm): 7.45 (d, J=7.8 Hz, 2H), 7.21 (d, J=9.3 Hz, 2H), 3.10 (s, 6H), 3.00 (s, 6H)

(Melting Point of Disulfide Compound)

Melting point: 140.4° C.

(LC-MS Analysis)

disulfide compound: M+H=496.99; trisulfide compound: M+H=528.96; tetrasulfide compound: M+H=560.94; pentasulfide compound: M+H=592.92

Example 3

Production of 4-Chloro-2-fluoro-5-mercaptophenyl N,N-Dimethylcarbamate

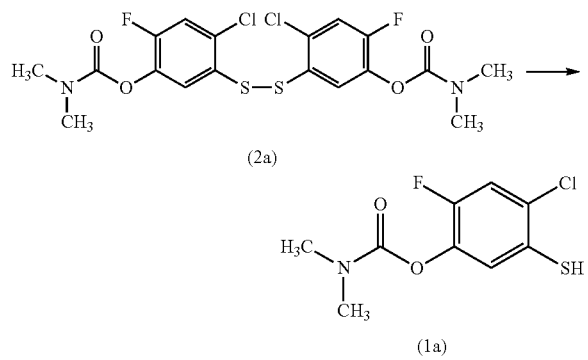

One-third (0.050 mol) of the toluene solution of bis(5-dimethylcarbamoyloxy-2-chloro-4-fluorophenyl) disulfide obtained in Example 2 was taken out and added to a 300 mL four-necked flask equipped with a stirrer, a reflux condenser, a thermometer, and a dropping funnel. Further, 25 mL of water, 10.6 g (0.100 mol) of sodium carbonate, and 0.645 g (0.001 mol) of a 50% tetrabutylammonium bromide aqueous solution were added at 10° C. While the mixture was stirred, an aqueous solution of 23.1 g (0.150 mol) of Rongalite dissolved in 100 mL of water was dropped at 10° C. over 1 h. Further, the mixture was stirred at 10° C. for 1 h. 15.6 g of 35% hydrochloric acid was dropped into the reaction mixture at 10° C. to adjust the pH of the reaction mixture to be 6.0 to 7.0. Then, the reaction mixture was separated into an organic layer and an aqueous layer to obtain 4-chloro-2-fluoro-5-mercaptophenyl N,N-dimethylcarbamate as a toluene solution. When the obtained toluene solution was subjected to LC analysis using a calibration curve, the yield of 4-chloro-2-fluoro-5-mercaptophenyl N,N-dimethylcarbamate was 70.6% (two steps).

$^1$H-NMR (300 MHz, CDCl3) δ (ppm): 7.214 (d, J=8.1 Hz, 1H), 7.212 (d, J=9.3 Hz, 1H), 3.82 (s, 1H), 3.10 (s, 3H), 3.01 (s, 3H)

Melting point: 81.1° C.

Example 4

Production of 4-Chloro-2-fluoro-5-mercaptophenol

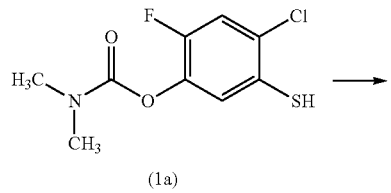

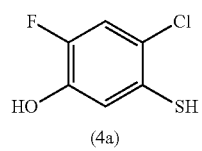

The toluene solution (0.0706 mol) of 4-chloro-2-fluoro-5-mercaptophenyl N,N-dimethylcarbamate obtained in Example 3 was added to a 200 mL four-necked flask equipped with a stirrer, a reflux condenser, a thermometer, and a dropping funnel. Further, 27.5 mL of water and 12.0 g (0.0750 mol) of a 25% sodium hydroxide aqueous solution were added to adjust the pH of the mixture to be 12 or higher. The mixture was stirred at 10° C. for 30 min and then separated into an organic layer and an aqueous layer. The obtained aqueous layer was washed with 12.5 mL of toluene to obtain a sodium salt aqueous solution of the raw material.

36.0 g (0.230 mol) of a 25% sodium hydroxide aqueous solution was added to a 200 mL four-necked flask equipped with a stirrer, a reflux condenser, a thermometer, and a dropping funnel, and heated to 80° C. The sodium salt aqueous solution of the raw material obtained above was dropped thereinto at 80° C. over 1 h, and further the mixture was stirred for 1 h.

20 mL of toluene and 31.2 g (0.300 mol) of 35% hydrochloric acid were added to a 200 mL four-necked flask equipped with a stirrer, a reflux condenser, a thermometer, and a dropping funnel, and the reaction mixture obtained above was dropped at room temperature over 1 h. The pH of the reaction mixture was adjusted to be 2 or lower, and then the reaction mixture was stirred at room temperature for 30 min. The reaction mixture was separated into an organic layer and an aqueous layer to obtain 4-chloro-2-fluoro-5-mercaptophenol as a toluene solution. When the obtained toluene solution was subjected to LC analysis using a calibration curve, the yield of 4-chloro-2-fluoro-5-mercaptophenol was 96.6%.

$^1$H-NMR (300 MHz, CDCl3) δ (ppm): 7.14 (d, J=5.1 Hz, 1H), 7.01 (d, J=4.4 Hz, 1H), 5.54 (bs, 1H), 3.81 (s, 1H)

Melting point: 65.1° C.

Example 5

Production of 2-Chloro-4-methylphenyl N,N-Dimethylcarbamate

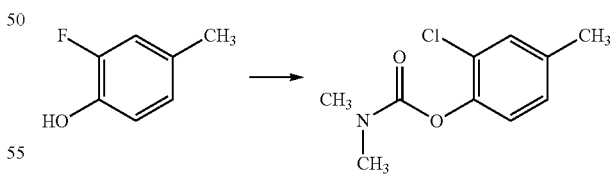

14.3 g (0.10 mol) of 2-chloro-4-methylphenol, 0.61 g (0.005 mol) of 4-dimethylaminopyridine, 12.9 g (0.12 mol) of dimethylcarbamoyl chloride, and 60 mL of dichloromethane were added to a 250 mL four-necked flask equipped with a stirrer, a reflux condenser, a thermometer, and a dropping funnel, and stirred. After the mixture was dissolved, 13.2 g (0.13 mol) of triethylamine was dropped at room temperature over 1 h, and further the mixture was stirred at room temperature for 5 h. The end of the reaction was confirmed. 20 mL of water and 3.1 g of 35% hydrochloric acid were added to the reaction mixture, and the mixture was stirred at room temperature for 30 min. Then, the mixture was separated into an organic layer and an aqueous layer, and 20 mL of water and 19.1 g of a 5% sodium hydrogen carbonate aqueous solution were added to the obtained organic layer. The mixture was stirred at room temperature for 30 min to wash the organic layer. Then, the mixture was separated into an organic layer and an aqueous layer, and for the obtained organic layer, the dichloromethane was distilled off under reduced pressure at 60° C. to obtain 21.2 g (yield 99%) of 2-chloro-4-methylphenyl N,N-dimethylcarbamate.

$^1$H-NMR (300 MHz, CDCl3) δ (ppm): 7.23-7.22 (m, 1H), 7.09-7.03 (m, 2H), 3.14 (s, 3H), 3.02 (s, 3H), 2.32 (s, 3H)

Melting point: 27.1° C.

Reference Example 1

Production of 4-Chloro-2-fluorophenyl Methanesulfonate

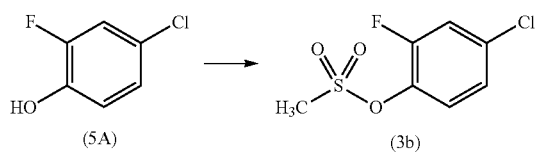

128 g (0.874 mol) of 4-chloro-2-fluorophenol, 110 g (0.961 mol) of mesyl chloride, and 224 mL of dichloromethane were added to a 1 L four-necked flask equipped with a stirrer, a reflux condenser, a thermometer, and a dropping funnel, and stirred. After the mixture was dissolved, 124 g (1.22 mol) of triethylamine was dropped at 10° C. over 1 h, and further the mixture was stirred at 10° C. for 1 h. The end of the reaction was confirmed. 367 mL of water and 79.6 g of 20% hydrochloric acid were added to the reaction mixture, and the mixture was stirred at room temperature for 30 min. Then, the mixture was separated into an organic layer and an aqueous layer. 197 mL of water was added to the obtained organic layer, and 173 g of an 8.5% sodium hydrogen carbonate aqueous solution was added. The mixture was stirred at room temperature for 30 min to wash the organic layer. The same washing operation was performed using 393 mL of water, and the obtained organic layer was subjected to azeotropic dehydration at 40 to 45° C. to obtain 4-chloro-2-fluorophenyl methanesulfonate as a dichloromethane solution. When the obtained dichloromethane solution was subjected to LC analysis using a calibration curve, the yield of 4-chloro-2-fluorophenyl methanesulfonate was 96.2%.

$^1$H-NMR (300 MHz, CDCl3) δ (ppm): 7.37-7.30 (m, 1H), 7.28-7.23 (m, 1H), 7.21-7.16 (m, 1H), 3.23 (d, J=0.73 Hz, 3H)

Melting point: 20.9° C.

Reference Example 2

Production of Bis(5-methanesulfonyloxy-2-chloro-4-fluorophenyl) Disulfide

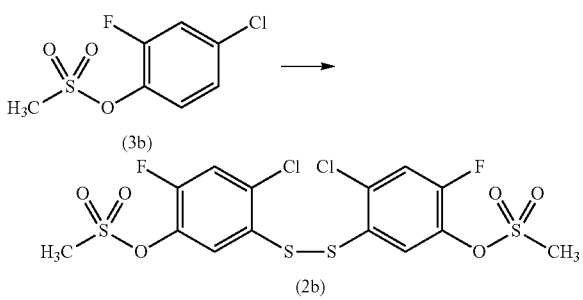

32.2 mL of dichloromethane and 16.0 g (0.120 mol) of aluminum chloride were added to a 100 mL four-necked flask equipped with a stirrer, a reflux condenser, a thermometer, and a dropping funnel. Next, while the mixture was stirred at room temperature, a solution of 18.0 g (0.08 mol) of 4-chloro-2-fluorophenyl methanesulfonate in 8 mL of dichloromethane was dropped. Then, 8.10 g (0.0600 mol) of sulfur monochloride was dropped into the mixture at 40° C. over 3 h, and further the mixture was stirred for 3 h.

74.5 mL of water and 32.2 mL of dichloromethane were added to a 200 mL four-necked flask equipped with a stirrer, a reflux condenser, a thermometer, and a dropping funnel, and the reaction mixture obtained above was dropped thereinto at room temperature. The mixture was stirred at room temperature for 30 min. Then, the mixture was separated into an organic layer and an aqueous layer, and 33.1 mL of water and 41.7 g of 35% hydrochloric acid were added to the obtained organic layer. The mixture was stirred for 30 min to wash the organic layer. The same washing operation was performed using each of 74.5 mL of water, 77.8 g of a 4% sodium hydrogen carbonate aqueous solution, and 74.5 g of water, and the mixture was separated into an organic layer and an aqueous layer. For the obtained organic layer, the dichloromethane was distilled off under reduced pressure at 80° C., and 80 mL of toluene was added to the obtained residue to obtain the target compound as a toluene solution.

$^1$H-NMR (300 MHz, CDCl3) δ (ppm): 7.63 (d, J=7.8 Hz, 2H), 7.32 (d, J=9.3 Hz, 2H), 3.20 (d, J=0.6 Hz, 6H)

Melting point: 154.7° C.

Reference Example 3

Production of 4-Chloro-2-fluoro-5-mercaptophenyl Methanesulfonate

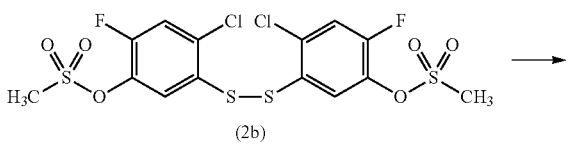

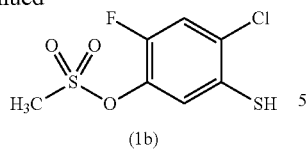

(1b)

The toluene solution (0.040 mol) of bis(5-methanesulfonyloxy-2-chloro-4-fluorophenyl) disulfide obtained in Reference Example 2 was added to a 300 mL four-necked flask equipped with a stirrer, a reflux condenser, a thermometer, and a dropping funnel. Further, 40 mL of water, 8.48 g (0.080 mol) of sodium carbonate, and 0.258 g (0.0008 mol) of tetrabutylammonium bromide were added at 10° C. While the mixture was stirred, an aqueous solution of 18.5 g (0.120 mol) of Rongalite dissolved in 80 mL of water was dropped at 10° C. over 1 h. Further, the mixture was stirred at 10° C. for 3 h. 16.7 g of 35% hydrochloric acid was dropped into the reaction mixture at 10° C. to adjust the pH of the reaction mixture to be 3.0 to 4.0. Then, the reaction mixture was separated into an organic layer and an aqueous layer to obtain 4-chloro-2-fluoro-5-mercaptophenyl methanesulfonate as a toluene solution.

$^1$H-NMR (300 MHz, CDCl3) δ (ppm): 7.39 (d, J=7.8 Hz, 1H), 7.30 (d, J=9.3 Hz, 1H), 3.91 (s, 1H), 3.24 (d, J=0.6 Hz, 3H)

Reference Example 4

Production of 4-Chloro-2-fluoro-5-mercaptophenol

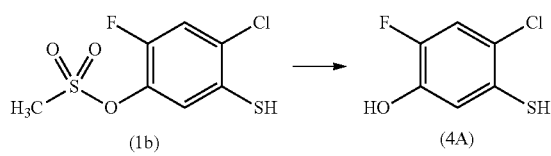

The toluene solution (0.08 mol) of 4-chloro-2-fluoro-5-mercaptophenyl methanesulfonate obtained in Reference Example 3 was added to a 200 mL four-necked flask equipped with a stirrer, a reflux condenser, a thermometer, and a dropping funnel. Further, an aqueous solution of 4.24 g (0.0400 mol) of sodium carbonate dissolved in 40 mL of water was added, and the mixture was stirred at room temperature for 30 min and then separated into an organic layer and an aqueous layer. The above extraction operation was repeated again, and the obtained aqueous layers were combined to obtain a sodium salt aqueous solution of the raw material.

32.0 g (0.200 mol) of a 25% sodium hydroxide aqueous solution was added to the obtained sodium salt aqueous solution, and the mixture was stirred at room temperature for 30 min. Then, 40 mL of toluene and 33.3 g (0.320 mol) of 35% hydrochloric acid were added to adjust the pH of the reaction mixture to be 2 or less. The reaction mixture was stirred at room temperature for 30 min and then separated into an organic layer and an aqueous layer to obtain 4-chloro-2-fluoro-5-mercaptophenol as a toluene solution. When the obtained toluene solution was subjected to LC analysis using a calibration curve, the yield of 4-chloro-2-fluoro-5-mercaptophenol was 42.7% (three steps).

$^1$H-NMR (300 MHz, CDCl3) δ (ppm): 7.14 (d, J=5.1 Hz, 1H), 7.01 (d, J=4.4 Hz, 1H), 5.54 (bs, 1H), 3.81 (s, 1H)
Melting point: 65.1° C.

Reference Production Example 1

Production of 4-Chloro-2-fluoro-5-(2,2,2-trifluoroethylthio)phenol

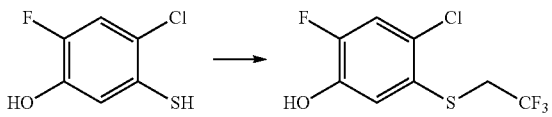 [SMILES: Oc1cc(S)c(Cl)cc1F ; Oc1cc(SCC(F)(F)F)c(Cl)cc1F]

(1) Production of 2,2,2-Trifluoroethyl p-Toluenesulfonate 28.6 mL of toluene, 10.9 g (0.109 mol) of trifluoroethanol, and 19.1 g (0.100 mol) of p-toluenesulfonic acid chloride were added to a 100 mL four-necked flask equipped with a stirrer, a reflux condenser, and a thermometer, and stirred at 60° C. to dissolution.

27.3 mL of toluene and 14.8 g (0.107 mol) of potassium carbonate were added to a 200 mL four-necked flask equipped with a stirrer, a reflux condenser, a thermometer, and a dropping funnel. The mixture obtained above was dropped thereinto at 40° C. over 1 h, and then 0.9 g of water was dropped in the same manner, and then the mixture was stirred at 40° C. for 1 h. After the end of the reaction was confirmed, 48.6 g of water was added to the reaction mixture, and the mixture was separated into an organic layer and an aqueous layer. For the obtained organic layer, the toluene was distilled off under reduced pressure at 60° C., and then 17.9 mL of DMF was added to the residue to obtain 2,2,2-trifluoroethyl p-toluenesulfonate as a DMF solution. When the obtained DMF solution was subjected to LC analysis using a calibration curve, the yield of 2,2,2-trifluoroethyl p-toluenesulfonate was 95.7%.

$^1$H-NMR (300 MHz, CDCl3) δ (ppm): 7.82 (m, 2H), 7.39 (m, 2H), 4.35 (q, J=7.9 Hz, 2H), 2.47 (s, 3H)

(2) Production of 4-Chloro-2-fluoro-5-(2,2,2-trifluoroethylthio)phenol 97.6 g (concentration: 47.6%, 0.260 mol) of the toluene solution of 4-chloro-2-fluoro-5-mercaptophenol obtained in Example 4 was added to a 1000 mL four-necked flask equipped with a stirrer, a reflux condenser, a thermometer, and a dropping funnel. The toluene was distilled off under reduced pressure at 60° C., and 65 mL of DMF was added to the residue. 160.3 g (concentration: 57.7%) of the DMF solution of 2,2,2-trifluoroethyl p-toluenesulfonate obtained in the above (1) was added to the mixture, and then 58.3 g (0.364 mol) of a 25% sodium hydroxide aqueous solution was dropped at 80° C. over 1 h, and further the mixture was stirred at 80° C. for 2 h. An aqueous solution of 4.01 g (0.0260 mol) of Rongalite dissolved in 17 mL of water was dropped thereinto at 80° C. over 1 h, and further the mixture was stirred at 80° C. for 2 h. 129 mL of toluene, 260 mL of water, and 31.2 g (0.195 mol) of a 25% sodium hydroxide aqueous solution were added to the obtained reaction mixture to adjust the pH of the reaction mixture to be 12 or higher. The reaction mixture was stirred at room temperature for 30 min and then separated into an organic layer and an aqueous layer, and the obtained aqueous layer was washed with 129 mL of toluene to obtain a sodium salt aqueous solution of the target compound.

260 mL of toluene and the sodium salt aqueous solution obtained above were added to a 1000 mL four-necked flask equipped with a stirrer, a reflux condenser, a thermometer, and a dropping funnel. 81.2 g (0.780 mol) of 35% hydrochloric acid was dropped thereinto at room temperature to adjust the pH of the mixture to be 4 or lower, and then the mixture was stirred at room temperature for 30 min. The reaction mixture was separated into an organic layer and an aqueous layer, and the obtained organic layer was washed with 130 mL of water to obtain 4-chloro-2-fluoro-5-(2,2,2-trifluoroethylthio)phenol as a toluene solution. When the obtained toluene solution was subjected to LC analysis using a calibration curve, the yield of 4-chloro-2-fluoro-5-(2,2,2-trifluoroethylthio)phenol was 93.2%.

$^1$H-NMR (300 MHz, CDCl3) δ (ppm): 7.27 (d, J=8.7 Hz, 1H), 7.22 (d, J=10.2 Hz, 1H), 5.15 (d, J=3.9 Hz, 1H), 3.43 (q, J=9.6 Hz, 2H)

INDUSTRIAL APPLICABILITY

According to the present invention, a novel method for producing a mercaptophenol compound useful as an intermediate for the synthesis of an agrochemical compound, and novel production intermediates are provided.

According to the present invention, a production method in which a mercaptophenol compound is obtained using an industrially preferred sulfur atom introduction reaction without using a chlorosulfonylation reaction for the introduction of a sulfur atom, and intermediate compounds of the mercaptophenol compound are provided.

According to the present invention, an intermediate compound having high crystallinity for which the choices of filtration and/or recrystallization are provided as an isolation method and/or a purification method is provided.

The mercaptophenol compound produced in the present invention is industrially useful as intermediates for the production of the excellent pest control agents disclosed in Patent Literatures 1, 2, and 3.

For example, a compound having excellent pest control activity can be derived from the 4-chloro-2-fluoro-5-mercaptophenol produced in Example 4 by forming 4-chloro-2-fluoro-5-(2,2,2-trifluoroethylthio)phenol according to the method described in Reference Production Example 1 and then performing a reaction disclosed in International Publication No. WO 2013/157229 and the like.

Therefore, the present invention has high industrial utility value.

The invention claimed is:

1. A 5-mercaptophenyl carbamate compound represented by formula (1):

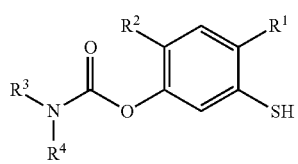

wherein $R^1$ and $R^2$ each independently represent a $C_1$-$C_4$ alkyl group or a halogen atom, $R^3$ and $R^4$ each independently represent a hydrogen atom, a $C_1$-$C_6$ alkyl group that may be substituted with one or two or more identical or different halogen atoms, a $C_2$-$C_6$ alkenyl group that may be substituted with one or two or more identical or different halogen atoms, a $C_3$-$C_6$ cycloalkyl group that may be substituted with one or two or more identical or different halogen atoms, a $C_1$-$C_6$ alkoxy group that may be substituted with one or two or more identical or different halogen atoms, a $C_6$-$C_{10}$ aryl group that may be substituted with one or two or more identical or different substituents A, or a $C_6$-$C_{10}$ aryl $C_1$-$C_4$ alkyl group that may be substituted with one or two or more identical or different substituents A, or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B, the substituent A represents a $C_1$-$C_4$ alkyl group or a halogen atom, and the substituent B represents a $C_1$-$C_4$ alkyl group, a halogen atom, or an oxo group.

2. The compound according to claim 1, wherein in the formula (1), $R^1$ and $R^2$ each independently represent a methyl group, a fluorine atom, or a chlorine atom, and $R^3$ and $R^4$ each independently represent a methyl group, an ethyl group, a propyl group, or an isopropyl group.

3. A poly sulfide compound represented by formula (2):

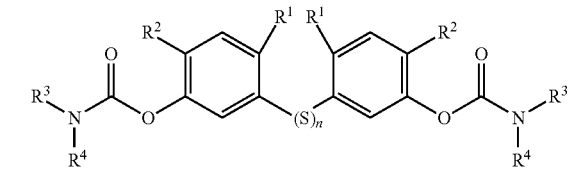

wherein $R^1$ and $R^2$ each independently represent a $C_1$-$C_4$ alkyl group or a halogen atom, $R^3$ and $R^4$ each independently represent a hydrogen atom, a $C_1$-$C_6$ alkyl group that may be substituted with one or two or more identical or different halogen atoms, a $C_2$-$C_6$ alkenyl group that may be substituted with one or two or more identical or different halogen atoms, a $C_3$-$C_6$ cycloalkyl group that may be substituted with one or two or more identical or different halogen atoms, a $C_1$-$C_6$ alkoxy group that may be substituted with one or two or more identical or different halogen atoms, a $C_6$-$C_{10}$ aryl group that may be substituted with one or two or more identical or different substituents A, or a $C_6$-$C_{10}$ aryl $C_1$-$C_4$ alkyl group that may be substituted with one or two or more identical or different substituents A, or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —(C$_1$-C$_3$ alkylene)-NH—(C$_1$-C$_3$ alkylene)- group that may be substituted with one or two or more identical or different substituents B, the substituent A represents a C$_1$-C$_4$ alkyl group or a halogen atom, the substituent B represents a C$_1$-C$_4$ alkyl group, a halogen atom, or an oxo group, and n represents an integer of 2 or more, or a mixture thereof.

4. The polysulfide compound or the mixture thereof according to claim 3, wherein in the formula (2), R$^1$ and R$^2$ each independently represent a methyl group, a fluorine atom, or a chlorine atom, R$^3$ and R$^4$ each independently represent a methyl group, an ethyl group, a propyl group, or an isopropyl group, and n represents an integer in the range of 2 to 6.

5. A method for producing a polysulfide compound represented by formula (2):

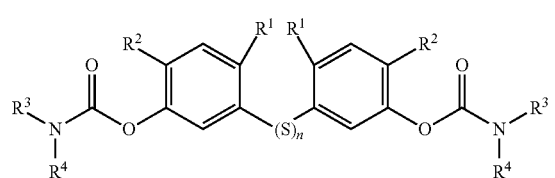

(2)

wherein R$^1$ and R$^2$ each independently represent a C$_1$-C$_4$ alkyl group or a halogen atom, R$^3$ and R$^4$ each independently represent a hydrogen atom, a C$_1$-C$_6$ alkyl group that may be substituted with one or two or more identical or different halogen atoms, a C$_2$-C$_6$ alkenyl group that may be substituted with one or two or more identical or different halogen atoms, a C$_3$-C$_6$ cycloalkyl group that may be substituted with one or two or more identical or different halogen atoms, a C$_1$-C$_6$ alkoxy group that may be substituted with one or two or more identical or different halogen atoms, a C$_6$-C$_{10}$ aryl group that may be substituted with one or two or more identical or different substituents A, or a C$_6$-C$_{10}$ aryl C$_1$-C$_4$ alkyl group that may be substituted with one or two or more identical or different substituents A, or R$^3$ and R$^4$ may together form a 4- to 8-membered ring by forming a divalent group selected from the group consisting of a C$_3$-C$_7$ alkylene group that may be substituted with one or two or more identical or different substituents B, a —(C$_1$-C$_3$ alkylene)-O—(C$_1$-C$_3$ alkylene)- group that may be substituted with one or two or more identical or different substituents B, and a —(C$_1$-C$_3$ alkylene)-NH—(C$_1$-C$_3$ alkylene)- group that may be substituted with one or two or more identical or different substituents B, the substituent A represents a C$_1$-C$_4$ alkyl group or a halogen atom, the substituent B represents a C$_1$-C$_4$ alkyl group, a halogen atom, or an oxo group, and n represents an integer of 2 or more, or a mixture thereof, comprising the following steps:

(i) a step of reacting a compound represented by formula (5):

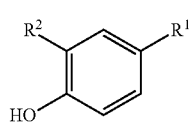

(5)

wherein R$^1$ and R$^2$ are as defined above, with a carbamoyl halide compound represented by formula (a):

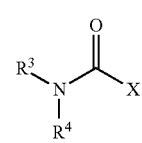

(a)

wherein R$^3$ and R$^4$ are as defined above, and X represents a halogen atom, in the presence of a base to produce a compound represented by formula (3):

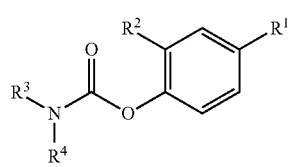

(3)

wherein R$^1$, R$^2$, R$^3$, and R$^4$ are as defined above; and (ii) a step of subjecting the compound represented by the formula (3) to a reaction with a sulfur compound in the presence of an acid to produce the compound represented by the formula (2).

6. The method according to claim 5, wherein R$^1$ and R$^2$ each independently represent a methyl group, a fluorine atom, or a chlorine atom, R$^3$ and R$^4$ each independently represent a methyl group, an ethyl group, a propyl group, or an isopropyl group, n represents an integer in the range of 2 to 6, and X represents a chlorine atom.

7. The method according to claim 5, wherein the base used in the step (i) is triethylamine, diisopropylethylamine, 1,8-diazabicyclo[5.4.0]-7-undec-7-ene (DBU), 1,4-diazabicyclo[2.2.2]octane (DABCO), N,N-dimethylaniline, N,N-diethylaniline, pyridine, 4-(dimethylamino)-pyridine, 2,6-lutidine, or a mixture thereof.

8. The method according to claim 5, wherein the acid used in the step (ii) is a Lewis acid.

9. A method for producing a 5-mercaptophenyl carbamate compound represented by formula (1):

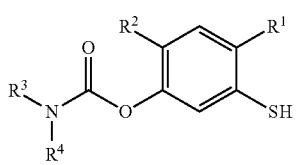

(1)

wherein $R^1$ and $R^2$ each independently represent a $C_1$-$C_4$ alkyl group or a halogen atom, $R^3$ and $R^4$ each independently represent a hydrogen atom, a $C_1$-$C_6$ alkyl group that may be substituted with one or two or more identical or different halogen atoms, a $C_2$-$C_6$ alkenyl group that may be substituted with one or two or more identical or different halogen atoms, a $C_3$-$C_6$ cycloalkyl group that may be substituted with one or two or more identical or different halogen atoms, a $C_1$-$C_6$ alkoxy group that may be substituted with one or two or more identical or different halogen atoms, a $C_6$-$C_{10}$ aryl group that may be substituted with one or two or more identical or different substituents A, or a $C_6$-$C_{10}$ aryl $C_1$-$C_4$ alkyl group that may be substituted with one or two or more identical or different substituents A, or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B, the substituent A represents a $C_1$-$C_4$ alkyl group or a halogen atom, and the substituent B represents a $C_1$-$C_4$ alkyl group, a halogen atom, or an oxo group, comprising the following steps:

(i) a step of reacting a compound represented by formula (5):

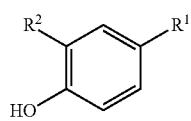

(5)

wherein $R^1$ and $R^2$ are as defined above, with a carbamoyl halide compound represented by formula (a):

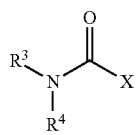

(a)

wherein $R^3$ and $R^4$ are as defined above, and X represents a halogen atom, in the presence of a base to produce a compound represented by formula (3):

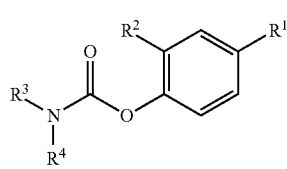

(3)

wherein $R^1$, $R^2$, $R^3$, and $R^4$ are as defined above;

(ii) a step of subjecting the compound represented by the formula (3) to a reaction with a sulfur compound in the presence of an acid to produce a polysulfide compound represented by formula (2):

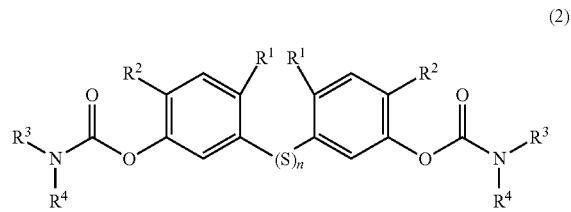

(2)

wherein $R^1$, $R^2$, $R^3$, and $R^4$ are as defined above, and n represents an integer of 2 or more, or a mixture thereof; and (iii) a step of producing the compound represented by the formula (1) from the compound represented by the formula (2).

10. The method according to claim 9, wherein $R^1$ and $R^2$ each independently represent a methyl group, a fluorine atom, or a chlorine atom, $R^3$ and $R^4$ each independently represent a methyl group, an ethyl group, a propyl group, or an isopropyl group, n represents an integer in the range of 2 to 6, and X represents a chlorine atom.

11. The method according to claim 9, wherein the base used in the step (i) is triethylamine, diisopropylethylamine, 1,8-diazabicyclo[5.4.0]-7-undec-7-ene (DBU), 1,4-diazabicyclo[2.2.2]octane (DABCO), N,N-dimethylaniline, N,N-diethylaniline, pyridine, 4-(dimethylamino)-pyridine, 2,6-lutidine, or a mixture thereof.

12. The method according to claim 9, wherein the acid used in the step (ii) is a Lewis acid.

13. A method for producing a mercaptophenol compound represented by formula (4):

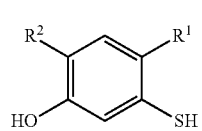

(4)

wherein $R^1$ and $R^2$ each independently represent a $C_1$-$C_4$ alkyl group or a halogen atom, comprising the following steps:

(i) a step of reacting a compound represented by formula (5):

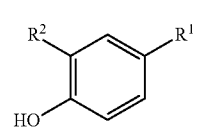

(5)

wherein $R^1$ and $R^2$ are as defined above,
with a carbamoyl halide compound represented by formula (a):

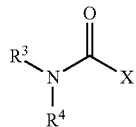
(a)

wherein $R^3$ and $R^4$ each independently represent a hydrogen atom, a $C_1$-$C_6$ alkyl group that may be substituted with one or two or more identical or different halogen atoms, a $C_2$-$C_6$ alkenyl group that may be substituted with one or two or more identical or different halogen atoms, a $C_3$-$C_6$ cycloalkyl group that may be substituted with one or two or more identical or different halogen atoms, a $C_1$-$C_6$ alkoxy group that may be substituted with one or two or more identical or different halogen atoms, a $C_6$-$C_{10}$ aryl group that may be substituted with one or two or more identical or different substituents A, or a $C_6$-$C_{10}$ aryl $C_1$-$C_4$ alkyl group that may be substituted with one or two or more identical or different substituents A,
or $R^3$ and $R^4$ may together form a 4- to 8-membered ring by forming a divalent group selected from the group consisting of a $C_3$-$C_7$ alkylene group that may be substituted with one or two or more identical or different substituents B, a —($C_1$-$C_3$ alkylene)-O—($C_1$-$C_3$ alkylene)- group that may be substituted with one or two or more identical or different substituents B, and a —($C_1$-$C_3$ alkylene)-NH—($C_1$-$C_3$ alkylene)- group that may be substituted with one or two or more identical or different substituents B,
the substituent A represents a $C_1$-$C_4$ alkyl group or a halogen atom,
the substituent B represents a $C_1$-$C_4$ alkyl group, a halogen atom, or an oxo group, and
X represents a halogen atom,
in the presence of a base to produce a compound represented by formula (3):

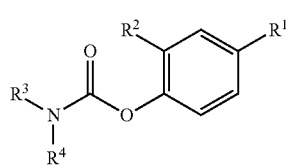
(3)

wherein $R^1$, $R^2$, $R^3$, and $R^4$ are as defined above;
(ii) a step of subjecting the compound represented by the formula (3) to a reaction with a sulfur compound in the presence of an acid to produce a compound represented by formula (2):

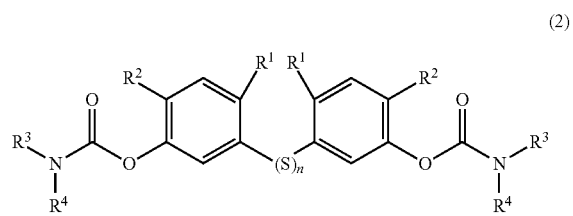
(2)

wherein $R^1$, $R^2$, $R^3$, and $R^4$ are as defined above, and n represents an integer of 2 or more;
(iii) a step of producing a compound represented by formula (1):

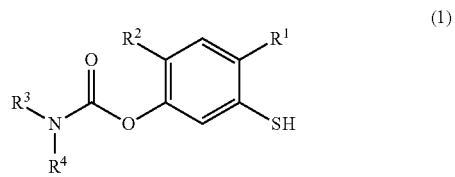
(1)

wherein $R^1$, $R^2$, $R^3$, and $R^4$ are as defined above,
from the compound represented by the formula (2); and
(iv) a step of producing the compound represented by the formula (4) from the compound represented by the formula (1).

14. The method according to claim 13, wherein $R^1$ and $R^2$ each independently represent a methyl group, a fluorine atom, or a chlorine atom,
$R^3$ and $R^4$ each independently represent a methyl group, an ethyl group, a propyl group, or an isopropyl group,
n represents an integer in the range of 2 to 6, and
X represents a chlorine atom.

15. The method according to claim 13, wherein the base used in the step (i) is triethylamine, diisopropylethylamine, 1,8-diazabicyclo[5.4.0]-7-undec-7-ene (DBU), 1,4-diazabicyclo[2.2.2]octane (DABCO), N,N-dimethylaniline, N,N-diethylaniline, pyridine, 4-(dimethylamino)-pyridine, 2,6-lutidine, or a mixture thereof.

16. The method according to claim 13, wherein the acid used in the step (ii) is a Lewis acid.

* * * * *